US012051487B2

(12) United States Patent
Fisher et al.

(10) Patent No.: US 12,051,487 B2
(45) Date of Patent: Jul. 30, 2024

(54) SYSTEMS AND METHODS FOR SUPPLEMENTING DATA WITH GENERATIVE MODELS

(71) Applicant: Unlearn.AI, Inc., San Francisco, CA (US)

(72) Inventors: Charles Kenneth Fisher, Truckee, CA (US); Aaron Michael Smith, Corte Madera, CA (US); Jonathan Ryan Walsh, El Cerrito, CA (US)

(73) Assignee: Unlearn.AI, Inc., San Francisco, CA (US)

( * ) Notice: Subject to any disclaimer, the term of this patent is extended or adjusted under 35 U.S.C. 154(b) by 283 days.

(21) Appl. No.: 16/997,758

(22) Filed: Aug. 19, 2020

(65) Prior Publication Data

US 2021/0057108 A1 Feb. 25, 2021

Related U.S. Application Data

(60) Provisional application No. 62/891,240, filed on Aug. 23, 2019.

(51) Int. Cl.
| | | |
|---|---|---|
| *G16H 10/20* | (2018.01) | |
| *A61B 5/00* | (2006.01) | |
| *G06N 3/02* | (2006.01) | |
| *G06N 5/02* | (2023.01) | |
| *G06N 7/01* | (2023.01) | |

(Continued)

(52) U.S. Cl.
CPC ........... *G16H 10/20* (2018.01); *A61B 5/4848* (2013.01); *G06N 3/02* (2013.01); *G06N 5/02* (2013.01); *G06N 7/01* (2023.01); *G16H 10/60* (2018.01); *G16H 50/20* (2018.01); *G16H 50/50* (2018.01);

(Continued)

(58) Field of Classification Search
CPC ........ G16H 10/00–80/00; G06N 3/00–99/007; A61B 1/00–2576/026
See application file for complete search history.

(56) References Cited

U.S. PATENT DOCUMENTS

| | | | |
|---|---|---|---|
| 7,634,464 B2 | 12/2009 | Chen et al. | |
| 8,150,629 B2 * | 4/2012 | Geerts | G16H 50/50 |
| | | | 703/11 |

(Continued)

FOREIGN PATENT DOCUMENTS

| | | | | |
|---|---|---|---|---|
| CA | 3088204 A1 * | 7/2019 | ........... | G06N 3/0445 |
| CN | 111758108 A | 10/2020 | | |

(Continued)

OTHER PUBLICATIONS

Balzer et al., "Adaptive pair-matching in randomized trials with unbiased and efficient effect estimation," Statist. Med. 2015, 34 999-1011; DOI: 10.1002/sim.6380. (Year: 2015).*

(Continued)

*Primary Examiner* — Jonathon A. Szumny
(74) *Attorney, Agent, or Firm* — KPPB LLP

(57) ABSTRACT

Systems and methods for determining treatment effects of a randomized control trial (RCT) in accordance with embodiments of the invention are illustrated. One embodiment includes a method for determining treatment effects. The method includes steps for receiving data from a RCT, generating result data using a set of one or more generative models, and determining treatment effects for the RCT using the generated result data.

20 Claims, 12 Drawing Sheets

(51) Int. Cl.
*G06N 20/00* (2019.01)
*G16H 10/60* (2018.01)
*G16H 50/20* (2018.01)
*G16H 50/50* (2018.01)
*G16H 50/70* (2018.01)
*G16H 70/20* (2018.01)

(52) U.S. Cl.
CPC .............. *G16H 50/70* (2018.01); *G16H 70/20* (2018.01); *G06N 20/00* (2019.01)

(56) References Cited

U.S. PATENT DOCUMENTS

| | | | |
|---|---|---|---|
| 9,495,582 B2 | 11/2016 | Guissin et al. | |
| 10,398,389 B1* | 9/2019 | D'Alessandro | A61B 5/14532 |
| 10,650,929 B1* | 5/2020 | Beck | G06F 16/55 |
| 10,726,954 B2* | 7/2020 | Su | G16H 50/20 |
| 11,120,528 B1 | 9/2021 | Seely et al. | |
| 11,501,429 B2 | 11/2022 | Stamatoyannopoulos et al. | |
| 11,574,462 B1 | 2/2023 | Bhatia et al. | |
| 11,636,309 B2 | 4/2023 | Fisher et al. | |
| 2004/0193019 A1* | 9/2004 | Wei | G16H 50/70 600/300 |
| 2005/0080462 A1 | 4/2005 | Jenkins et al. | |
| 2008/0082359 A1* | 4/2008 | Jung | G16B 20/00 705/2 |
| 2009/0326976 A1* | 12/2009 | Morris | G06Q 40/08 705/2 |
| 2010/0235310 A1 | 9/2010 | Gage et al. | |
| 2010/0254973 A1* | 10/2010 | Mohapatra | A61P 11/06 435/7.1 |
| 2011/0218817 A1* | 9/2011 | Spiegel | G16H 10/20 705/2 |
| 2014/0019059 A1* | 1/2014 | Shankle | G16H 50/20 702/19 |
| 2014/0046683 A1 | 2/2014 | Michelson et al. | |
| 2014/0257128 A1 | 9/2014 | Moxon et al. | |
| 2015/0010610 A1* | 1/2015 | Tom | A61K 35/50 435/1.1 |
| 2016/0140300 A1* | 5/2016 | Purdie | G16H 10/60 705/2 |
| 2016/0180053 A1* | 6/2016 | Fuertinger | G16H 50/50 705/2 |
| 2016/0222448 A1 | 8/2016 | Horvath | |
| 2017/0161635 A1 | 6/2017 | Oono et al. | |
| 2017/0286627 A1* | 10/2017 | Barhak | G16H 50/50 |
| 2017/0344706 A1 | 11/2017 | Torres et al. | |
| 2017/0357844 A1* | 12/2017 | Comaniciu | G16H 50/20 |
| 2017/0372193 A1 | 12/2017 | Mailhe et al. | |
| 2018/0018590 A1* | 1/2018 | Szeto | G16H 40/20 |
| 2018/0046780 A1 | 2/2018 | Graiver et al. | |
| 2018/0081914 A1 | 3/2018 | Zoll et al. | |
| 2018/0315505 A1* | 11/2018 | Itu | G16H 10/20 |
| 2018/0336319 A1 | 11/2018 | Itu et al. | |
| 2019/0019570 A1* | 1/2019 | Fuertinger | G16H 50/50 |
| 2019/0220733 A1 | 7/2019 | Fisher et al. | |
| 2019/0303471 A1 | 10/2019 | Lee et al. | |
| 2020/0035362 A1* | 1/2020 | Abou Shousha | G16H 50/20 |
| 2020/0357490 A1* | 11/2020 | Kartoun | G16H 10/20 |
| 2020/0395103 A1* | 12/2020 | Ramakrishnan | G06F 16/31 |
| 2020/0411199 A1* | 12/2020 | Shrager | G16H 15/00 |
| 2021/0090694 A1 | 3/2021 | Colley et al. | |
| 2021/0117842 A1 | 4/2021 | Smith et al. | |
| 2021/0158906 A1 | 5/2021 | Xie et al. | |
| 2021/0241860 A1 | 8/2021 | Bhattacharya et al. | |
| 2021/0353203 A1* | 11/2021 | Burman | G16H 50/30 |
| 2022/0157413 A1 | 5/2022 | Fisher et al. | |
| 2022/0172085 A1 | 6/2022 | Fisher et al. | |
| 2022/0318689 A1 | 10/2022 | Li-Bland et al. | |
| 2022/0344009 A1 | 10/2022 | Schuler da Costa Ferro | |
| 2022/0415454 A1 | 12/2022 | Schuler da Costa Ferro et al. | |
| 2023/0004796 A1 | 1/2023 | Mayer et al. | |
| 2023/0209035 A1 | 6/2023 | Kaabi et al. | |
| 2023/0245777 A1 | 8/2023 | Foschini et al. | |
| 2023/0352125 A1 | 11/2023 | Fisher | |
| 2023/0352138 A1 | 11/2023 | Fisher | |

FOREIGN PATENT DOCUMENTS

| | | | | |
|---|---|---|---|---|
| CN | 112863622 | A | 5/2021 | |
| CN | 113724806 | A | 11/2021 | |
| EP | 3740908 | A1 | 11/2020 | |
| EP | 4018394 | A1 | 6/2022 | |
| EP | 4220650 | A1 | 8/2023 | |
| JP | 2021511584 | A | 5/2021 | |
| JP | 202231730 | A | 2/2022 | |
| JP | 2022544859 | A | 10/2022 | |
| JP | 7305656 | B2 | 6/2023 | |
| WO | WO-2006084196 | A2 * | 8/2006 | ........... G06F 19/324 |
| WO | 2007022020 | A2 | 2/2007 | |
| WO | 2007022020 | A3 | 6/2007 | |
| WO | 2016145379 | A1 | 9/2016 | |
| WO | 2019143737 | A1 | 7/2019 | |
| WO | 2020154573 | A1 | 7/2020 | |
| WO | 2021003485 | A1 | 1/2021 | |
| WO | 2021041128 | A1 | 3/2021 | |
| WO | 2021077097 | A1 | 4/2021 | |
| WO | WO-2022101809 | A1 * | 5/2022 | |
| WO | 2022120350 | A2 | 6/2022 | |
| WO | 2022120350 | A3 | 8/2022 | |
| WO | WO-2022187064 | A1 * | 9/2022 | |
| WO | 2022272308 | A1 | 12/2022 | |
| WO | 2019143737 | A8 | 3/2023 | |
| WO | 2023212734 | A1 | 11/2023 | |

OTHER PUBLICATIONS

Ventz et al., "Design and Evaluation of an External Control Arm Using Prior Clinical Trials and Real-World Data," Clin Cancer Res 2019; 25:4993-5001; doi: 10.1158/1078-0432.CCR-19-0820. (Year: 2019).*

Cui et al., "Multilevel modeling and value of information in clinical trial decision support," BMC Systems Biology (2014) 8:6; DOI 10.1186/s12918-014-0140-0. (Year: 2014).*

Karcher et al., "The "RCT augmentation": a novel simulation method to add patient heterogeneity into phase III trials," BMC Medical Research Methodology (2018) 18:75; https://doi.org/10.1186/s12874-018-0534-6. (Year: 2018).*

International Preliminary Report on Patentability for International Application PCT/US2019/013870, Report issued Jul. 21, 2020, Mailed Jul. 30, 2020, 4 Pgs.

International Search Report and Written Opinion for International Application No. PCT/US2019/013870, Search completed Mar. 18, 2019, Mailed Mar. 27, 2019, 9 Pgs.

International Search Report and Written Opinion for International Application No. PCT/US2020/047054, Search completed Oct. 8, 2020, Mailed Nov. 23, 2020, 10 Pgs.

Akhtar et al., "Improving the Robustness of Neural Networks Using K-Support Norm Based Adversarial Training," IEEE Access; Publication [online], Dec. 28, 2016, pp. 1-9.

Arici et al., "Associative Adversarial Networks," arXiv:1611.06953v1 [cs.LG], Nov. 18, 2016, 8 pgs.

Arjovsky et al., "Wasserstein GAN," arXiv:1701.07875v1 [stat.ML], Jan. 26, 2017, 30 pgs.

Bengio et al., "Greedy Layer-Wise Training of Deep Networks," Advances in Neural Information Processing Systems, 2007, 13 pgs.

Chatterjee et al., "Explaining Complex Distributions with Simple Models," 2008. Econophysics. pp. 1-15.

Cho et al., "Gaussian-Bernoulli deep Boltzmann machine," Proceedings of the 2013 International Joint Conference on Neural Networks (IJCNN), Dallas, Texas, Aug. 4-9, 2013, 9 pgs.

Dutt et al., "Generative Adversarial Networks (GAN) Review," CVR Journal of Science and Technology, Dec. 2017, vol. 13, pp. 1-5.

Fisher et al., "Boltzmann Encoded Adversarial Machines," preprint arXiv:1804.08682, 2018, 17 pgs.

(56) References Cited

OTHER PUBLICATIONS

Gabrie et al., "Training Restricted Boltzmann Machines via the Thouless-Anderson-Palmer Free Energy," Advances in Neural Information Processing Systems, vol. 28, 2015, 9 pgs.
Goodfellow et al., "Generative Adversarial Nets," Advances in Neural Information Processing Systems, vol. 27, 2014, 9 pgs.
Greydanus, "Generative Adversarial Networks for the Mnist dataset," "Mnist gan," http://github.com/greydanus/mnist-gan (2017), 2 pgs.
Hinton, "A Fast Learning Algorithm for Deep Belief Nets," Neural Computation 18, pp. 1527-1554 (2006).
Hinton, "A Practical Guide to Training Restricted Boltzmann Machines," Neural networks: Tricks of the trade, pp. 599-619. Springer, Berlin, Heidelberg, 2012.
Hinton et al., "Reducing the Dimensionality of Data with Neural Networks," Science, vol. 313, No. 5786, Jul. 28, 2006, pp. 504-507.
Kullback et al., "On Information and Sufficiency," The Annals of Mathematical Statistics, vol. 22, No. 1, 1951, pp. 79-86.
Li et al., "Temperature based Restricted Boltzmann Machines," Scientific Reports Jan. 13, 2016, vol. 19133, 12 pages, DOI:10.1038/srep19133.
Lopez-Ruiz et al., "Equiprobability, Entropy, Gamma Distributions and Other Geometrical Questions in Multi-Agent Systems," Entropy, 2009, vol. 11, pp. 959-971, doi:10.3390/e11040959.
Montavon et al., "Wasserstein Training of Restricted Boltzmann Machines," Advances in Neural Information Processing Systems, vol. 29, 2016, 9 pgs.
Nguyen et al., "Latent Patient Profile Modelling and Applications with Mixed-Variate Restricted Boltzmann Machine," Advances in Knowledge Discovery and Data Mining, 2013, pp. 123-135.
Nguyen et al., "Supervised Restricted Boltzmann Machines," UAI. 2017, 10 pgs.
Rogers et al., "Combining patient-level and summary-level data for Alzheimer's disease modeling and simulation: a beta regression meta-analysis," Journal of Pharmacokinetics and Pharmacodynamics, 2012, vol. 39, pp. 479-498, DOI 10.1007/s10928-012-9263-3.
Salakhutdinov et al., "Deep Boltzmann Machines," Proc. International Conference on Artificial Intelligence and Statistics, 2009, pp. 448-455.
Sutskever et al., "The Recurrent Temporal Restricted Boltzmann Machine," Advances in Neural Information Processing Systems, 2009, pp. 1601-1608.
Tran et al., "Mixed-Variate Restricted Boltzmann Machines," Asian Conference on Machine Learning, JMLR: Workshop and Conference Proceedings 20, 2011, pp. 213-229.
Tuzman, Karen Tkach, "Broadening role for external control arms in clinical trials," Biocentury, Tools & Techniques, reprint from Jul. 15, 2019, 5 pgs.
Zhang et al., "Predictive Deep Boltzmann Machine for Multiperiod Wind Speed Forecasting," IEEE Transactions on Sustainable Energy, 2015, vol. 6, Issue 4, pp. 1416-1425, doi: 10.31109/TSTE.2015.244387.
Extended European Search Report for European Application No. 19741291.9, Search completed Sep. 8, 2021, Mailed Sep. 17, 2021, 12 Pgs.
International Preliminary Report on Patentability for International Application PCT/US2020/047054, Report issued Feb. 17, 2022, Mailed on Mar. 3, 2022, 5 Pgs.
Grover et al., "Flow-GAN: Combining Maximum Likelihood and Adversarial Learning in Generative Models," arXiv:1705.08868, May 24, 2017, 10 pages.
Kim et al., "Deep Directed Generative Models with Energy-Based Probability Estimation," arXiv:1606.03439, Jun. 10, 2016, 9 pages.
Liu et al., "A Survey of Deep Neural Network Architectures and their Applications," Neurocomputing, vol. 234, Apr. 19, 2017, pp. 11-26.
Miotto et al., "Deep Learning for Healthcare: Review, Opportunities and Challenges," Briefings in Bioinformatics, vol. 19, No. 6, 2017, 11 pgs.
International Search Report and Written Opinion for International Application No. PCT/US2022/073165, Search completed Aug. 14, 2022, Mailed Sep. 7, 2022, 9 pgs.
International Search Report and Written Opinion for International Application PCT/US2021/072678, search completed Jan. 31, 2022, Mailed Jul. 1, 2022, 13 Pgs.
Lamb et al., "GibbsNet: Iterative Adversarial Inference for Deep Graphical Models", arXiv preprint arXiv:1712.04120v1, 2017, 11 pgs.
Royston, "A Combined Test for a Generalized Treatment Effect in Clinical Trials with a Time-to-Event Outcome", The Stata Journal, 2017, 17, No. 2, pp. 405-421.
Royston et al., "A Simulation Study Comparing the Power of Nine Tests of the Treatment Effect in Randomized Controlled Trials with a Time-to-Event Outcome", Royston and Parmar Trials (2020). Retrieved on Aug. 14, 2022. Retrieved from <URL: https://link.springer.com/content/pdf/10.1186/s13063-020-4153-2.pdf> entire document.
Royston et al., "Augmenting the Logrank Test in the Design of Clinical Trials in which Non-Proportional Hazards of the Treatment Effect may be Anticipated", Royston and Parmar BMC Medical Research Methodology (2016). Retrieved on Aug. 14, 2022. Retrieved from <URL:https://bmcmedresmethodol.biomedcentral.conn/track/pdf/10.1186/s12874-016-0110-x.pdf> entire document.
Song et al., "Generative Adversarial Learning of Markov Chains", Accessed at URL https://openreview.net/forum?id=S1L-hCNtl, 2017, 7 Pages.
Yu et al., "Assessment and adjustment of approximate inference algorithms using the law of total variance", arXiv preprint arXiv:1911.08725, Nov. 2019 [online], [retrieved on Jan. 31, 2022].
International Preliminary Report on Patentability for International Application PCT/US2020/056354, Report issued Apr. 19, 2022, Mailed on Apr. 28, 2022, 05 Pgs.
International Preliminary Report on Patentability for International Application PCT/US2021/072678, Report issued May 30, 2023, Mailed on Jun. 15, 2023, 08 Pgs.
International Search Report and Written Opinion for International Application No. PCT/US2020/056354, Search completed Dec. 21, 2020, Mailed Jan. 25, 2021, 09 pgs.
"Procova™ Handbook for the Target Trial Statistician", Ver. 1.0, Dec. 29, 2021, European Medicines Agency.
Burges et al., "Learning to Rank Using Gradient Descent", Proceedings of the 22nd International Conference on Machine Learning, 2005, 8 pages.
Coon et al., "A High-Density Whole-Genome Association Study Reveals That APOE Is the Major Susceptibility Gene for Sporadic Late-Onset Alzheimer's Disease", The Journal of Clinical Psychiatry, 2007, vol. 68, No. 04, pp. 613-618, 2007, doi: 10.4088/jcp.v68n0419.
Davidian et al., "Semiparametric Estimation of Treatment Effect in a Pretest-Posttest Study", Biometrics, Dec. 2003, vol. 59, No. 4, pp. :1046-1055, 2003. ISSN 0006-341X. doi: 10.1111/ j.0006-341x.2003.00120.x.
Eickhoff et al., "Copulas for Information Retrieval", Proceedings of the 36th International ACM SIGIR Conference on Research and Development in Information Retrieval, Jul. 2013, pp. 663-672.
Hannan, , "Randomized Clinical Trials and Observational Studies: Guidelines for Assessing Respective Strengths and Limitations", JACC: Cardiovascular Interventions, Jun. 2008, vol. 1, No. 3, pp. 211-217, https://doi.org/10.1016/j.jcin.2008.01.008.
Maldonado, , "Estimating causal effects", International Journal of Epidemiology, Apr. 2002, vol. 31, No. 2, pp. 422-429.
Neville et al., "Development of a unified clinical trial database for Alzheimer's disease", Alzheimer's & Dementia: The Journal of the Alzheimer's Association, 2015, vol. 11, No. 10, pp. 1212-1221, https://doi.org/10.1016/j.jalz.2014.11.005.
Quinn et al., "Docosahexaenoic Acid Supplementation and Cognitive Decline in Alzheimer Disease: A Randomized Trial", Journal of the American Medical Association, Nov. 3, 2010, vol. 304, No. 17, pp. 1903-1911, doi: 10.1001/jama.2010.1510.
Romano et al., "Resurrecting weighted least squares", Journal of Econometrics, 197(1), 48 pgs., Available at: https://doi.org/10.1016/j.jeconom.2016.10.003.

(56) References Cited

OTHER PUBLICATIONS

Romero et al., "The coalition against major diseases: developing tools for an integrated drug development process for alzheimer's and parkinson's diseases", Clinical Pharmacology & Therapeutics, Aug. 12, 2009, vol. 86, No. 4, pp. 365-367, https://doi.org/10.1038/clpt.2009.165.

Rosen et al., "A New Rating Scale for Alzheimer's Disease", American Journal of Psychiatry, Nov. 1984, vol. 141, Issue 11, pp. 1356-1364, https://doi.org/10.1176/ajp.141.11.1356.

Rubin, "Causal Inference Using Potential Outcomes: Design, Modeling, Decisions", Journal of the American Statistical Association, Mar. 2005, vol. 100, No. 469, pp. 322-331, https://doi.org/10.1198/016214504000001880.

Schuler et al., "Increasing the efficiency of randomized trial estimates via Linear Adjustment for a prognostic score", The International Journal of Biostatistics, 18(2), pp. 329-356. Available at: https://doi.org/10.1515/ijb-2021-0072.

Sox et al., "The Methods of Comparative Effectiveness Research", Annual Review of Public Health, Apr. 2012, vol. 33, pp. 425-445, doi: 10.1146/annurev-publhealth-031811-124610.

Extended European Search Report for European Application No. 20857028.3, Search completed Aug. 11, 2023, Mailed Aug. 21, 2023, 12 Pgs.

Extended European Search Report for European Application No. 23154548.4, Search completed Jun. 15, 2023, Mailed Jun. 23, 2023, 11 Pgs.

International Search Report and Written Opinion for International Application No. PCT/US2023/066412, Search completed Aug. 16, 2023, Mailed Sep. 13, 2023, 14 Pgs.

Allison, "Handling Missing Data by Maximum Likelihood", SAS Global Forum 2012: Statistics and Data Analysis, 21 pages.

Graham et al., "Analysis with missing data in drug prevention research", NIDA Research Monograph, Feb. 1994, vol. 142, pp. 13-63.

Gupta, "Intention-to-treat concept: a review", Perspectives in Clinical Research, Jul. 2011, vol. 2, No. 3, pp. 109-112, doi: 10.4103/2229-3485.83221.

Jerez et al., "Missing data imputation using statistical and machine learning methods in a real breast cancer problem", Artificial Intelligence in Medicine, (Year: 2010), vol. 50, Issue 2.

Lipton et al., "Modeling missing data in clinical time series with rnns", Machine Learning for Healthcare. Jun.3, 2016;56(56):253-70.

Liu et al., "Image inpainting for irregular holes using partial convolutions", Proceedings of the European conference on computer vision (ECCV), 2018, pp. 85-100.

Marlin et al., "Recommender systems: Missing data and statistical model estimation", Proceedings of the Twenty-Second international joint conference on Artificial Intelligence, 2011, vol. Three (IJCAI'11), AAAI Press, pp. 2686-2691.

Shan et al., "Accurate Unconditional p-Values for a Two-Arm Study with Binary Endpoints", Journal of Statistical Computation and Simulation, [Online] Apr. 13, 2018, vol. 88, No. 6, pp. 1200-1210, XP093073190, ISSN: 0094-9655, DOI: 10.1080/00949655.2018. 1425690, Retrieved from the Internet: URL:https://www.ncbi.nlm.nih.gov/pmc/articles/PMC6510515/pdf/nihms-1504617.pdf> [retrieved on Jan. 28, 2018].

Shan et al., "Exact p-Values for Simon's Two-Stage Designs in Clinical Trials", Statistics in Biosciences, Springer US, Boston, [Online]Jun. 16, 2016, vol. 8, No. 2, pp. 351-357, XP036062971, ISSN: 1867-1764, DOI:10.1007/S12561-016-9152-1, Retrieved from the Internet: URL:https://www.ncbi.nlm.nih.gov/pmc/articles/PMC5167475/>.

Silva et al., "Predicting In-Hospital Mortality of ICU Patients: The PhysioNet/Computing in Cardiology Challenge 2012", Computing in Cardiology, 2012, vol. 39, pp. 245-248.

Sterne et al., "Multiple imputation for missing data in epidemiological and clinical research: potential and pitfalls", BMJ, 2009, pp. 338, doi: https://doi.org/10.1136/bmj.b2393 (Published Jun. 29, 2009).

Tipirneni et al., "Self-supervised transformer for sparse and irregularly sampled multivariate clinical time-series", ACM Transactions on Knowledge Discovery from Data (TKDD), 2022, vol. 16, No. 6, pp. 1-17.

Yi et al., "ST-MVL: Filling Missing Values in Geo-Sensory Time Series Data", Proceedings of the Twenty-Fifth International Joint Conference on Artificial Intelligence, 2016, pp. 2704-2710.

International Preliminary Report on Patentability for International Application PCT/US2022/073165, Report issued Dec. 14, 2023, Mailed on Jan. 4, 2024, 6 pgs.

"Critical Path Institute (C-Path) Online Data Repository (CODR)", Critical Path For Alzheimer's Disease, 2023, 5 pgs.

"Digital twin generators", Unlearn.AI, 2024, 5 pgs.

"E9(r1) statistical principles for clinical trials: Addendum: Eestimands and sensitivity analysis in clinical trials", US Department of Health and Human Services, Food and Drug Administration, Center for Drug Evaluation and Research (CDER), Center for Biologics Evaluation and Research (CBER), and ICH (2021), 23 pgs.

Andersen et al., "Generalised linear models for correlated pseudo-observations, with applications to multi-state models", Biometrika, vol. 90, Issue 1, Mar. 2003, pp. 15-27, https://doi.org/10.1093/biomet/90.1.15.

Carroll et al., "The effect of estimating weights in weighted least squares", Journal of the American Statistical Association, vol. 83, No. 404, 1988, pp. 1045-1054.

Cohen-Mansfield, "Agitated behaviors in the elderly: II. Preliminary results in the cognitively deteriorated.", Journal of the American Gerontological Society, vol. 34, Issue 10, Oct. 1986, pp. 722-727.

Cummings et al., "The Neuropsychiatric Inventory: comprehensive assessment of psychopathology in dementia", Neurology, vol. 44, No. 12, 1994, pp. 2308-2314.

Davidian et al., "Guideline on Adjustment for Baseline Covariates in Clinical Trials", European Medicines Agency, 2015, 11 pgs.

Davidian et al., "Qualification Opinion for Prognostic Covariate Adjustment", European Medicines Agency, 2022, 33 pgs.

Davidian et al., "Variance function estimation", Journal of the American Statistical Association, vol. 82, No. 400, Dec. 1987, pp. 1079-1091.

Fisher, "A rule of thumb for the power gain due to covariate adjustment in randomized controlled trials with continuous outcomes", Aug. 9, 2023, arXiv:2308.07330, 1 pg.

Fisher, "On the mathematical foundations of theoretical statistics", Philosophical Transactions of the Royal Society of London. Series A, Containing Papers of a Mathematical or Physical Character, Jan. 1, 1922, vol. 222, Issue 594-604, pp. 309-368.

Fisher, "Statistical Methods for Research Workers", Oliver and Boyd, 5th Edition, 1934.

Folstein et al., "Mini-mental state: A practical method for grading the cognitive state of patients for the clinician", Journal of Psychiatric Research, vol. 12, No. 3, 1975, pp. 189-198.

Folstein et al., "Adjusting for Covariates in Randomized Clinical Trials for Drugs and Biological Products: Guidance for Industry", Food and Drug Administration, US Department of Health and Human Services, Center for Drug Evaluation and Research (CDER), and Center for Biologics Evaluation and Research (CBER), 2023, 12 pgs.

Freedman, "On the So-Called "Huber Sandwich Estimator" and "Robust Standard Errors"", The American Statistician, vol. 60, No. 4, 2006, pp. 299-302.

Freedman, "Randomization Does Not Justify Logistic Regression", Statistical Science, 2008, vol. 23, No. 2, pp. 237-249.

Galasko et al., "An inventory to assess activities of daily living for clinical trials in Alzheimer's disease", Alzheimer's Disease and Associated Disorders, vol. 11, 1997, Suppl 2, pp. S33-S39.

Graw et al., "On pseudo-values for regression analysis in competing risks models", Lifetime Data Analysis, Dec. 3, 2008, vol. 15, pp. 241-255, DOI 10.1007/s10985-008-9107-z.

Hariton et al., "Randomised controlled trials—the gold standard for effectiveness research", BJOG: An International Journal of Obstetrics & Gynaecology, Jun. 19, 2018, vol. 125, No. 13, pp. 1716-1716.

Holland, "Statistics and causal inference", Journal of the American Statistical Association, vol. 81, No. 396, 1986, pp. 945-960.

(56) References Cited

OTHER PUBLICATIONS

Imbens et al., "Causal Inference for Statistics, Social, and Biomedical Sciences: An Introduction", Cambridge University Press, 2015, pp. 1365-1366.
Jacobsen et al., "A Note on the Large Sample Properties of Estimators Based on Generalized Linear Models for Correlated Pseudo-observations", Scandinavian Journal of Statistics, vol. 43, No. 3, Feb. 23, 2016, pp. 845-862.
Joiner, "Lurking variables: Some examples", The American Statistician, vol. 35, No. 4, 1981, pp. 227-233.
Kempthorne et al., "Design and Analysis of Experiments", Wiley, 1952.
Lang et al., "Neural Boltzmann Machines", arXiv:2305.08337, 2023, 7 pgs.
Little et al., "Statistical Analysis With Missing Data", Wiley, 2019.
MacKinnon et al., "Some heteroskedasticity-consistent covariance matrix estimators with improved finite sample properties", Journal of Econometrics, vol. 29, No. 3, 1985, pp. 305-325.
Meloun et al., "Linear Regression Models", Statistical Data Analysis, 2011, pp. 449-629.
Morris, "The Clinical Dementia Rating (CDR): Current version and scoring rules", Neurology, vol. 43, No. 11, 1993, pp. 2412-2414.
Safieh et al., "ApoE4: an emerging therapeutic target for alzheimer's disease", BMC Medicine, vol. 17, No. 64, 2019, pp. 1-17.
Schneider et al., "ADCS Prevention Instrument Project: ADCS-clinician's global impression of change scales (ADCS-CGIC), self-rated and study partner-rated versions", Alzheimer's Disease and Associated Disorders, vol. 20, No. 4, 2006, Suppl 3, pp. S124-S138.
Smith, "Introducing Unlearn's new Digital Twin Generation Architecture", accessed at https://unlearnai.substack.com/p/introducing-unlearns-new-digital on 2023, 5 pgs.
Splawa-Neyman, "On the Application of Probability Theory to Agricultural Experiments. Essay on Principles. Section 9", Nov. 1990, Statistical Science, vol. 5, No. 4, pp. 465-472.
Steinbach, "The jackknife, the bootstrap, and censored data: A review and simulation study", University of Minnesota, Technical Report No. 411, Nov. 1982, 25 pgs.
Tariot et al., "Chronic Divalproex Sodium to Attenuate Agitation and Clinical Progression of Alzheimer Disease", Archives of General Psychiatry, vol. 68, No. 8, 2011, pp. 853-861.
Tian et al., "Predicting the restricted mean event time with the subject's baseline covariates in survival analysis", Biostatistics, 2014, vol. 15, No. 2, pp. 222-233.
Turner et al., "A randomized, double-blind, placebo-controlled trial of resveratrol for alzheimer disease", Neurology, vol. 85, No. 16, 2015, pp. 1383-1391.
Walsh, "Introducing an updated digital twin generator for Alzheimer's disease", Unlearn.AI, 2023, 2 pgs.
Wang et al., "Data-driven and probabilistic learning of the process-structure-property relationship in solution-grown tellurene for optimized nanomanufacturing of high-performance nanoelectronics", Nano Energy, vol. 57, Mar. 2019, pp. 480-491.
Weisberg, "Applied Linear Regression", John Wiley & Sons, 4th edition, 2014, 370 pgs.
White, "A heteroskedasticity-consistent covariance matrix estimator and a direct test for heteroskedasticity", Econometrica, vol. 48, No. 4, 1980, pp. 817-838.

* cited by examiner

SYSTEMS AND METHODS FOR SUPPLEMENTING DATA WITH GENERATIVE MODELS

CROSS-REFERENCE TO RELATED APPLICATIONS

The current application claims the benefit of and priority under 35 U.S.C. § 119(e) to U.S. Provisional Patent Application No. 62/891,240 entitled "System and Method for Supplementing Data in Randomized Controlled Trials with Generative Models" filed Aug. 23, 2019. The disclosure of U.S. Provisional Patent Application No. 62/891,240 is hereby incorporated by reference in its entirety for all purposes.

FIELD OF THE INVENTION

The present invention generally relates to supplementing data for analysis and, more specifically, to using generative models to supplement data for analysis.

BACKGROUND

Randomized Controlled Trials (RCTs) are commonly used to assess the safety and efficacy of new treatments, such as drugs and medical devices. In an RCT, a group of subjects with particular characteristics are randomly assigned to one or more experimental groups receiving new treatments or to a control group receiving a comparative treatment (e.g., a placebo), and the outcomes from these groups are compared in order to assess the safety and efficacy of the new treatments. It is expensive, time consuming and, in some cases, unethical to recruit human subjects to participate in RCTs.

SUMMARY OF THE INVENTION

Systems and methods for determining treatment effects of a randomized control trial (RCT) in accordance with embodiments of the invention are illustrated. One embodiment includes a method for determining treatment effects. The method includes steps for receiving data from a RCT, generating result data using a set of one or more generative models, and determining treatment effects for the RCT using the generated result data.

In a further embodiment, the received data includes panel data from subjects of the RCT and the generated result data includes predicted panel data for a set of one or more digital subjects. The panel data describes the observed values of multiple characteristics at multiple discrete timepoints.

In still another embodiment, the predicted panel data for the set of digital subjects is generated based on population statistics of the RCT and the generated result data is used to supplement control arm data of the RCT data.

In a still further embodiment, the predicted panel data for the set of digital subjects is generated based on individual characteristics of the subjects of the RCT.

In yet another embodiment, determining the treatment effects includes comparing the predicted panel data based on characteristics of a particular subject with the panel data for the particular subject from the RCT data.

In a yet further embodiment, the predicted panel data for a particular subject includes several predicted outcomes. Determining the treatment effects includes computing transformed tail-area probabilities based on the several predicted outcomes, and determining responses for the particular subject based on the transformed tail-area probabilities.

In another additional embodiment, the method further includes steps for receiving historical data. The historical data includes at least one of control arm data from historical control arms, patient registries, electronic health records, and real world data.

In a further additional embodiment, the method further includes steps for pre-training the set of generative models using the historical data.

In another embodiment again, the method further includes steps for determining a prior distribution based on the historical data. Determining the treatment effects is further based on the prior distribution.

In a further embodiment again, the method further includes steps for tuning a first generative model of the set of generative models using the RCT data for a control arm of the RCT and a second generative model of the set of generative models using the RCT data for a treatment arm of the RCT. Determining the treatment effects includes comparing the first and second generative models.

In still yet another embodiment, comparing the first and second generative models includes drawing a first set of samples from the first generative model, drawing a second set of samples from the second generative model, and comparing distributions of the first and second sets of samples.

In a still yet further embodiment, the method further includes steps for determining a set of characteristics for the RCT. The set of characteristics includes a number of subjects to be enrolled in each of a control arm and a treatment arm.

In still another additional embodiment, determining the set of characteristics for the RCT is based on at least one of a desired type-I error rate and a desired type-II error rate.

In a still further additional embodiment, the set of generative models includes at least one of a Conditional Restricted Boltzmann Machine, a statistical model, a generative adversarial network, a recurrent neural network, a Gaussian process, an autoencoders, an autoregressive model, and a variational autoencoder.

In still another embodiment again, determining the treatment effects comprises determining a bias for the set of generative models, and correcting the determined treatment effects based on the determined bias.

In a still further embodiment again, determining the treatment effects includes computing conditional average treatment effects based on interactions.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

DETAILED DESCRIPTION

Systems and methods in accordance with some embodiments of the invention can determine treatment effects for a randomized control trial (RCT) using data sampled from a generative model, design RCTs, and/or determine decision rules for treatments. Data sampled from generative models in accordance with some embodiments of the invention may be referred to as 'digital subjects' throughout this description. In many embodiments, digital subjects can be generated to match given statistics of the treatment groups at the beginning of the study. Digital subjects in accordance with numerous embodiments of the invention can be generated for each subject in a study and the generated digital subjects can be used as digital twins for a counterfactual analysis. In various embodiments, generative models can be used to compute a measure of response that is individual to each patient and this response can be used to assess the effect of the treatment. Systems and methods in accordance with several embodiments of the invention can correct for bias that may be introduced by incorporating generated digital subject data.

In certain embodiments, processes in accordance with a number of embodiments of the invention can improve RCT design by reducing the number of subjects required for different arms of the RCT. Processes in accordance with some embodiments of the invention can improve the ability of a system to accurately determine treatment effects from a RCT by increasing the statistical power of the trial. In many embodiments, the process of conducting a RCT can be improved from the design through the analysis and treatment decisions.

Figure 1:
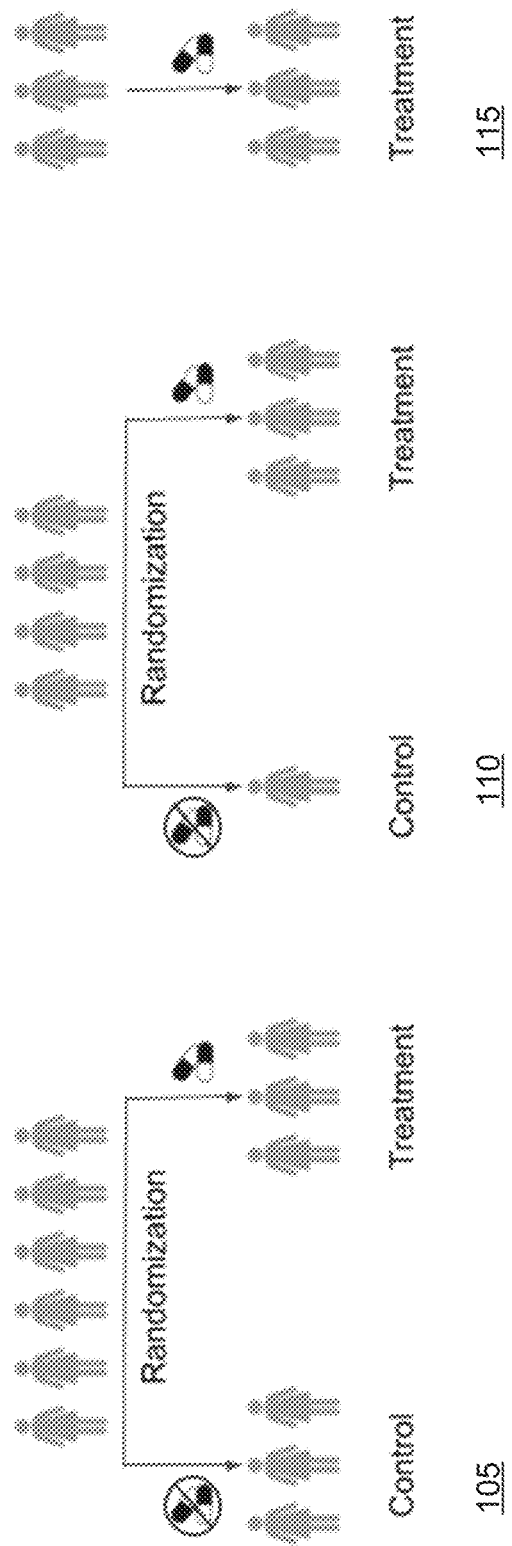
FIG. 1 illustrates examples of uses for generative models in the analysis of clinical trials in accordance with various embodiments of the invention.

Examples of uses for generative models in the analysis of clinical trials in accordance with various embodiments of the invention are illustrated in FIG. 1. The first example 105 illustrates that generative models, digital subjects, or digital twins can be used to increase the statistical power of traditional randomized controlled trials. In the second example 110, generated data is used to decrease the number of subjects required to be enrolled in the control group of a randomized controlled trial. The third example 115 shows that generated can be used as the external comparator arm of a single-arm trial.

In an RCT, a group of subjects with particular characteristics are randomly assigned to one or more experimental groups receiving new treatments or to a control group receiving a comparative treatment (e.g., a placebo), and the outcomes from these groups can be compared in order to assess the safety and efficacy of the new treatments. Without loss of generality, an RCT can be assumed to include i=1, . . . , N human subjects. These subjects are often randomly assigned to a control group or to a treatment group such that the probability of being assigned to the treatment group is the same for each subject regardless of any unobserved characteristics. The assignment of subject i to a group is represented by an indicator variable $w_i$. For example, in a study with two groups $w_i=0$ if subject i is assigned to the control group and $w_i=1$ if subject i is assigned to the treatment group. The number of subjects assigned to the treatment group is $N_T=\Sigma_i w_i$ and the number of subjects assigned to the control group is $N_C=N-N_T$.

In various embodiments, each subject i in an RCT can be described by a vector $x_i(t)$ of variables $x_{ij}(t)$ at time t. In this description, the notation $X_i=\{x_i(t)\}_{t=1}^T$ denotes the panel of data from subject i and $x_{0,i}$ to denote the vector of data taken at time zero. An RCT is often concerned with estimating how a treatment affects an outcome $y_i=f(X_i)$. The function $f(\cdot)$ describes the combination of variables being used to assess the outcome of the treatment. Variables in accordance with a number of embodiments of the invention can include (but is not limited to) simple endpoints based on the value of a single variable at the end of the study, composite scores constructed from the characteristics of a patient at the end of the study, and/or time-dependent outcomes such as rates of range or survival times, among others. Approaches in accordance with various embodiments of the invention as described herein can be applied to analyze the effect of treatments on one or more outcomes (such as (but not limited to) those related to the efficacy and safety of the treatment).

Each subject has two potential outcomes. If the subject were to be assigned to the control group $w_i=0$, then $y_i^{(0)}$ would be the observed potential outcome. By contrast, if the subject were to be assigned to receive treatment $w_i=1$, then $y_i^{(1)}$ would be the observed potential outcome. In practice, a subject can only be assigned to one of the treatment arms such that the observed outcome is $Y_i=y_i^{(0)}(1-w_i)+w_i y_i^{(1)}$. Potential outcomes in accordance with many embodiments of the invention can include various measurements, such as, but not limited to conditional average treatment effect:

$$\tau(x_0)=E[Y|w=1,x_0]-E[Y|w=0,x_0] \quad (1)$$

and/or the average treatment effect $$\tau=E[\tau(x_0)]=E[Y|w=1]-E[Y|w=0]. \quad (2)$$

Processes in accordance with several embodiments of the invention can estimate these quantities with high accuracy and precision and/or can determine decision rules for declaring treatments to be effective that have low error rates.

It can be expensive, time consuming and, in some cases, unethical to recruit human subjects to participate in RCTs. As a result, a number of methods have been developed for using external control arms to reduce the number of subjects required for an RCT. These methods typically fall into two buckets referred to as 'historical borrowing' or 'external control'.

Historical borrowing refers to incorporating data from the control arms of previously completed trials into the analysis of a new trial. Typically, historical borrowing applies Bayesian methods using prior distributions derived from the historical dataset. Such methods can be used to increase the power of a randomized controlled trial, to decrease the size of the control arm, or even to replace the control arm with the historical data itself (i.e., an 'external control arm'). Some examples of external control arms include control arms from previously completed clinical trials (also called historical control arms), patient registries, and data collected from patients undergoing routine care (called real world data). Use of these external control arms can have serious drawbacks if the population or design of the current RCT differs from the population or design of the external data sources.

It has recently become possible to apply machine learning methods to create simulated subject records. In addition to data from the RCT, generative models in accordance with several embodiments of the invention can link the baseline characteristics $x_0$ and the control potential outcome $y^{(0)}$ through a joint probability distribution $p_{\theta_J}(y^{(0)}, x_0)$ and a conditional probability distribution $p_{\theta_C}(y^{(0)}|x_0)$, in which $\theta_J$ and $\theta_C$ are the parameters of the joint and conditional distributions, respectively. Note that a model of the joint distribution will also provide a model of the conditional distribution, but the converse is not true.

In several embodiments, simulated subject records can be sampled from probabilistic generative models that can be trained on various data, such as (but not limited to) one or more of historical, registry, and/or real world data. Such models can allow one to extrapolate to new patient populations and study designs.

In some embodiments, generative models may create data in a specialized format—either directly or indirectly—such as the Study Data Tabulation Model (SD™) to facilitate seamless integration into standard workflows. In a variety of embodiments, generating entire panels of data can be attractive because many of the trial outcomes (such as primary, secondary, and exploratory endpoints as well as safety information) can be analyzed in a parsimonious way using a single generative model. For simplicity, the notation $p(y,x_0)$ will be used instead of $p(X)$ in this description, with the understanding that the former can always be obtained from the latter by generating a panel of data X and then computing a specific outcome $y=f(X)$ from the panel.

Systems and methods in accordance with numerous embodiments of the invention can provide various approaches for incorporating data from a probabilistic generative model into the analysis of an RCT. In numerous embodiments, such methods can be viewed as borrowing from a model, as opposed to directly borrowing from a historical dataset. As generative models, from which data can be borrowed, may be biased (for example, due to incorrect modeling assumptions), systems and methods in accordance with a number of embodiments of the invention can account for these potential biases in the analysis of an RCT. Generative models in accordance with various embodiments of the invention can provide control over the characteristics of each simulated subject at the beginning of the study. For example, processes in accordance with various embodiments of the invention can create one or more digital twins for each human subject in the study. Processes in accordance with certain embodiments of the invention can incorporate digital twins to increase statistical power and can provide more individualized information than traditional study designs, such as study designs that borrow population level information or that use nearest neighbor matches to patients in historical or real world databases.

Determining Treatment Effects

Figure 2:
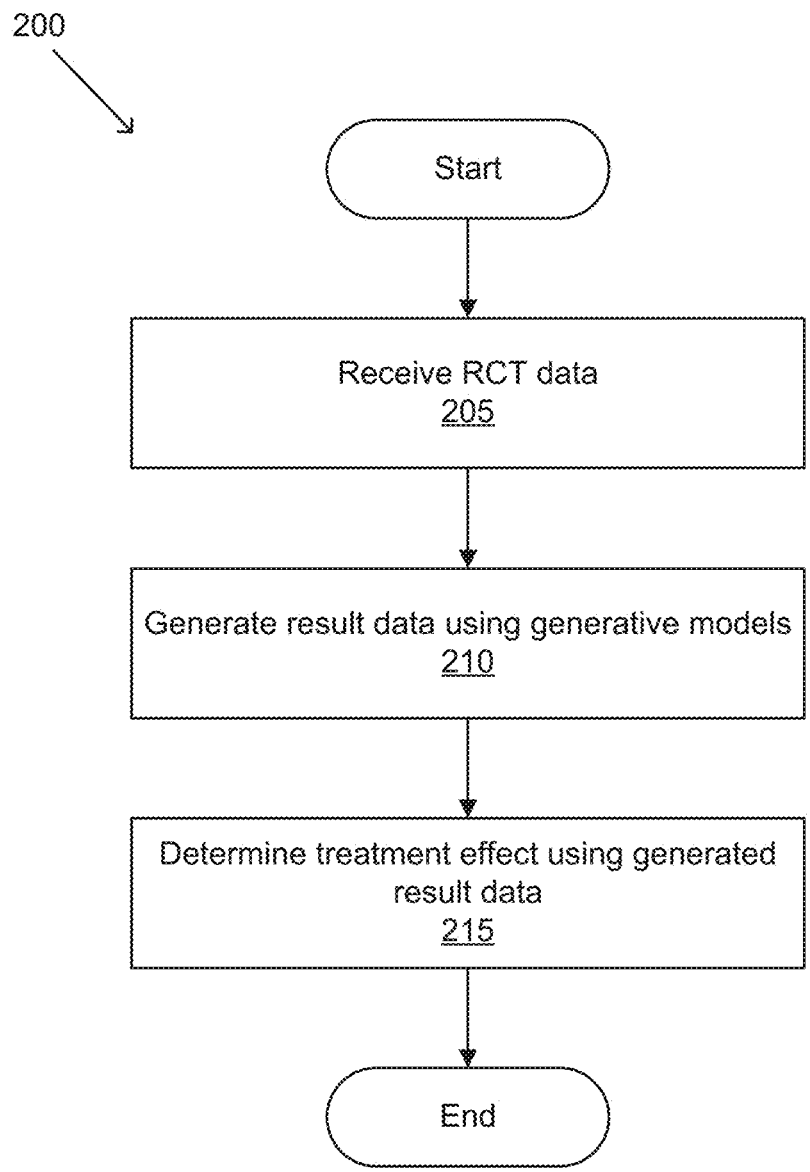
FIG. 2 conceptually illustrates an example of a process for determining treatment effects of a RCT in accordance with an embodiment of the invention.

An example of a process for determining treatment effects of a RCT is conceptually illustrated in FIG. 2. Process 200 receives (205) RCT data. RCT data can include panel data collected from subjects of a RCT. RCT data in accordance with a variety of embodiments of the invention can be divided into control and treatment arms based on whether subjects received a treatment. In many embodiments, RCT data can be supplemented with generated subject data. Generated subject data in accordance with a number of embodiments of the invention can include (but is not limited to) digital subject data and/or digital twin data.

In several embodiments, processes can receive historical data that can be used to pre-train generative models and/or to determine a prior distribution for Bayesian analyses. Historical data in accordance with numerous embodiments of the invention can include (but is not limited to) control arms from historical control arms, patient registries, electronic health records, and/or real world data.

Process 200 generates (210) digital subject data using generative models. Generative models in accordance with certain embodiments of the invention can be trained to generate potential outcome data based on characteristics of an individual and/or a population. Digital subject data in accordance with several embodiments of the invention can include (but is not limited to) panel data, outcome data, etc. In numerous embodiments, generative models can be trained directly on a specific outcome $p(y|x_0)$. For example, if a goal of using the generative model is to increase the statistical power for the primary analysis of a randomized controlled trial then it may be sufficient (but not necessary) to only use a model of $p(y|x_0)$.

Alternatively, or conjunctively, generative models trained to generate panel data that can be used in the analysis of a clinical trial. Data for a subject in a clinical trial is typically a panel; that is, it describes the observed values of multiple characteristics at multiple discrete timepoints (e.g. visits to the clinical trial site). For example, if a goal of using the generative model is to reduce the number of subjects in the control group of the trial, or as an external comparator for a single arm trial, then generated panel data in accordance with many embodiments of the invention can be used to perform many or all of the analyses of the trial.

In several embodiments, generative models can include (but are not limited to) traditional statistical models, generative adversarial networks, recurrent neural networks, Gaussian processes, autoencoders, autoregressive models, variational autoencoders, and/or other types of probabilistic generative models. For example, processes in accordance with several embodiments of the invention can use sequential models such as (but not limited to) a Conditional Restricted Boltzmann Machine for the full joint distribution of the panel data, $p(X)$, from which any outcome can be computed.

Figure 3:
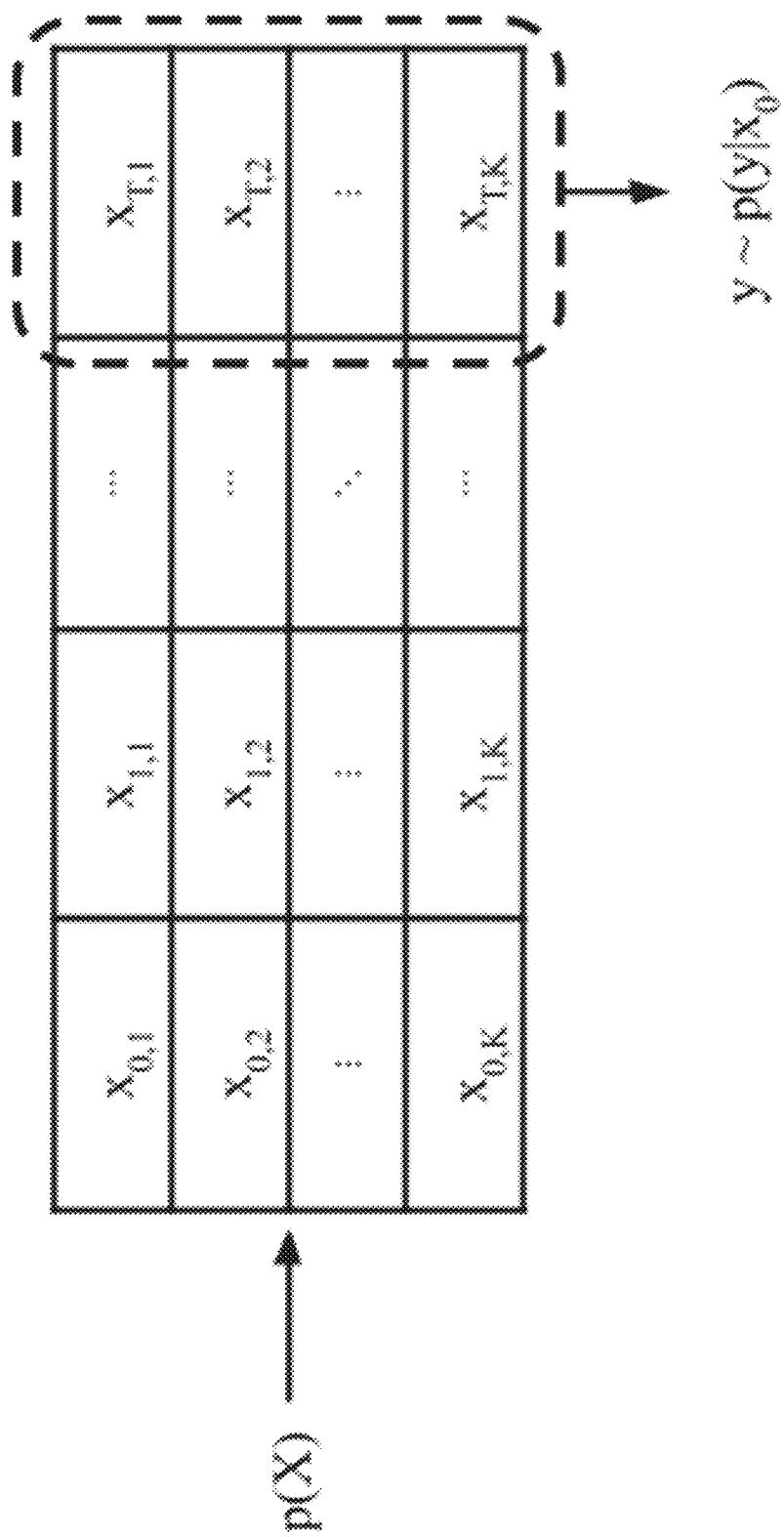
FIG. 3 illustrates an example of generative models for clinical trial panel data in accordance with an embodiment of the invention.

An example of generative models for clinical trial panel data in accordance with an embodiment of the invention is illustrated in FIG. 3. Generating panel data in accordance with a variety of embodiments of the invention can enable one to borrow information from the generative model for various analyses in the clinical trial (e.g., primary, secondary, and exploratory endpoints as well as safety information), not just one specific outcome. In addition, digital subjects drawn from the generative model can be of the same form as data obtained from actual subjects in the trial.

Referring back to FIG. 2, process 200 determines (215) treatment effects for the RCT using the generated digital subject data. Generative models in accordance with many embodiments of the invention can be incorporated into the analysis of an RCT in a variety of different ways for various applications. In many embodiments, generative models can be used to estimate treatment effect by training separate generative models based on data from the control and treatment arms. Processes in accordance with many embodiments of the invention can use generative models to generate digital subjects to supplement a control arm in an RCT. In certain embodiments, processes can use generative models to generate digital twins for individuals in the control and/or treatment arms. Generative models in accordance with numerous embodiments of the invention used to define individualized responses to treatment. Various methods for determining treatment effects in accordance with various embodiments of the invention are described in greater detail herein.

In several embodiments, treatment effects can be determined by fitting generalized linear models (GLMs) to the generated digital subject data and/or the RCT data. In a number of embodiments, multilevel GLMs can be set up so that the parameters (e.g., the treatment effect) can be estimated through maximum likelihood or Bayesian approaches. In a frequentist approach, one can test the null hypothesis $\beta_0=0$, whereas the Bayesian approach may focus on the posterior probability Prob($\beta_0 \geq 0$|data, prior).

While specific processes for determining treatment effects in an RCT are described above, any of a variety of processes can be utilized to determine treatment effects as appropriate to the requirements of specific applications. In certain embodiments, steps may be executed or performed in any order or sequence not limited to the order and sequence shown and described. In a number of embodiments, some of the above steps may be executed or performed substantially simultaneously where appropriate or in parallel to reduce latency and processing times. In some embodiments, one or more of the above steps may be omitted.

Estimating the Treatment Effect Using Generative Models

In many embodiments, processes can estimate treatment effects by training two new generative models: a treatment model using the data from the treatment group, $$p_{\theta_{J_1}}(y^{(1)}, x_0 | w_1),$$

and a control model using the data from the control group, $$p_{\theta_{J_0}}(y^{(0)}, x_0 | w_0).$$

In a variety of embodiments, full panels of data from an RCT can be used to train generative models to create panels of generated data. Such processes can allow for the analysis of many outcomes (including (but not limited to) primary, secondary, and exploratory efficacy endpoints as well as safety information) by comparing the trained treatment models against trained control models. For simplicity, the notation $p(y,x_0)$ will be used instead of $p(X)$, with the understanding that the former can always be obtained from the latter by generating a panel of data X and then computing a specific outcome $y=f(X)$ from the panel.

In one embodiment, generative models for the control condition (e.g., a Conditional Restricted Boltzmann Machine) can be trained on historical data from previously completed clinical trials. Then, two new generative models for the control and treatment groups can be obtained by solving minimization problems:

$$\min_{\theta_{J_0}} \left\{ -\sum_i (1-w_i) \log p_{\theta_{J_0}}(Y_i, x_{0,i} | w_0) + \lambda_0 D(p_{\theta_{J_0}}, p_{\theta_J}) \right\}$$

$$\min_{\theta_{J_1}} \left\{ -\sum_i w_i \log p_{\theta_{J_1}}(Y_i, x_{0,i} | w_1) + \lambda_1 D(p_{\theta_{J_1}}, p_{\theta_J}) \right\}$$

in which $\lambda_0$ and $\lambda_1$ are prior parameters that describe how well pre-trained generative models describe the outcomes in the two arms of the RCT, and $D(\cdot,\cdot)$ is a measure of the difference between two generative models such as (but not limited to) the Kullback-Leibler divergence. For example, the new generative models may also be Conditional Restricted Boltzmann Machines.

The estimate for the treatment effect can then be computed as $$\hat{\tau} = \int dy dx y p_{\theta_{J_1}}(y, x | w_1) - \int dy dx y p_{\theta_{J_0}}(y, x | w_0). \quad (3)$$

In several embodiments, treatment effects can be computed by drawing samples from the control and treatment models and comparing the distributions of the samples. Processes in accordance with some embodiments of the invention can further tune the computation of treatment effects by adjusting for the uncertainty in treatment effect estimates. In several embodiments, the uncertainty in treatment effect estimates ($\sigma_{\hat{\tau}}$) can be obtained using a bootstrap by repeatedly resampling the data from the RCT (with replacement), training the updated generative models, and computing an estimate for the treatment effect; the uncertainty is the standard deviation of these estimates. In a number of embodiments, point estimates for the treatment effect and the estimate for its uncertainty can be used to perform a hypothesis test in order to create a decision rule.

In numerous embodiments, processes can begin with a distribution $\pi(\theta_J)$ for the parameters of the generative model (e.g., obtained from a Bayesian analysis of historical data). Then, posterior distributions for $\theta_{J_0}$ and $\theta_{J_1}$ can be estimated by applying Bayes rule, $$\log \pi(\theta_{J_0}) = \text{constant} + \sum_i (1-w_i) p_{\theta_{J_0}}(Y_i, x_i | w_0) + \lambda_0 \log \pi(\theta_J) \quad (4)$$

$$\log \pi(\theta_{J_1}) = \text{constant} + \sum_i w_i p_{\theta_{J_1}}(Y_i, x_i | w_1) + \lambda_1 \log \pi(\theta_J).$$

In certain embodiments, point estimates for the treatment effect can be calculated as the mean of the posterior distribution $$\hat{\tau} = \int dy dx d\theta_{J_1} y p_{\theta_{J_1}}(y, x | w_1) \pi(\theta_{J_1}) - \quad (5)$$

-continued $$\int dy dx d\theta_{J_0} y p_{\theta_{J_0}}(y, x | w_0) \pi(\theta_{J_1}),$$

where the uncertainty is the variance of the posterior distribution $$\delta^2 \tau = \int dy dx d\theta_{J_1} y^2 p_{\theta_{J_1}}(y, x | w_1) \pi(\theta_{J_1}) - \quad (6)$$

$$\int dy dx d\theta_{J_0} y^2 p_{\theta_{J_0}}(y, x | w_0) \pi(\theta_{J_1}) - \hat{\tau}^2.$$

As above, point estimates for the treatment effect and estimates for their uncertainty can be used to perform a hypothesis test in order to create a decision rule in accordance with certain embodiments of the invention. Processes in accordance with a variety of embodiments of the invention can train conditional generative models $$p_{\theta_{J_1}}(y^{(1)} | x_0, w_1) \text{ and } p_{\theta_{J_0}}(y^{(0)}, | x_0, w_0),$$

as opposed to (or in conjunction with) joint generative models, in order to estimate treatment effects that are conditioned on the baseline covariates $x_0$.

It can be difficult to determine the operating characteristics of a decision rule based on these methods. Specifically, extensive simulations can be required in order to estimate the type-I error rate (i.e., the probability that an ineffective treatment would be declared to be effective) and the type-II error rate (i.e., the probability that an effective treatment would be declared ineffective). Well-characterized operating characteristics are required for many applications of RCTs and, as a result, this approach is often impractical. Generative models that rely on modern machine learning techniques are typically computationally expensive to train. As a result, using the bootstrap or Bayesian methods to obtain uncertainties required to formulate reasonable decision rules can be quite challenging.

Figure 4:
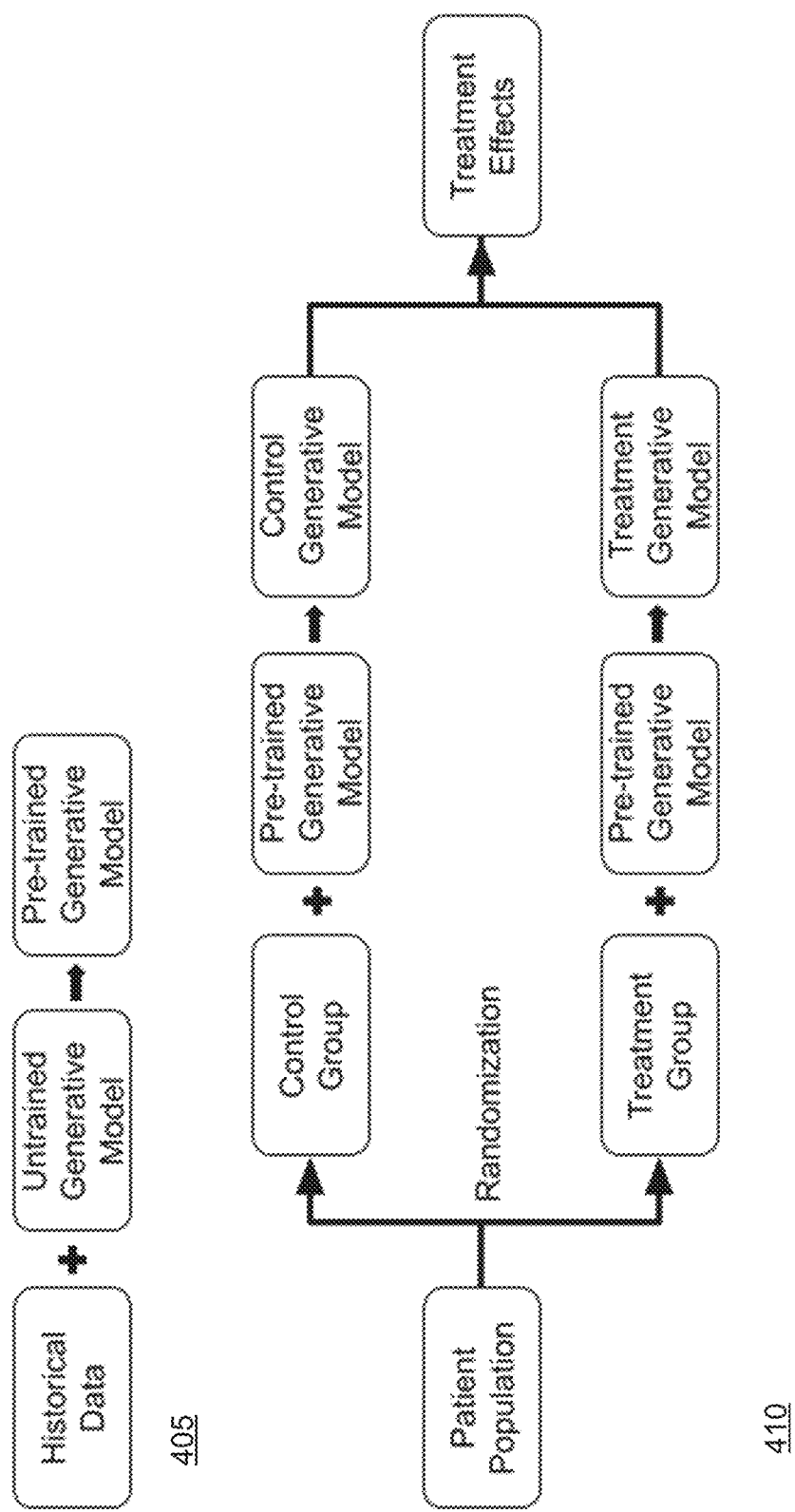
FIG. 4 illustrates an example of using generative models to estimate treatment effects in accordance with an embodiment of the invention.

An example of using generative models to estimate treatment effects in accordance with an embodiment of the invention is illustrated in FIG. 4. In the first stage 405, an untrained generative model of the control condition is trained using historical data, such as (but not limited to), data from previously completed clinical trials, electronic health records, and/or other studies. In the second stage 410, a patient population is randomly divided into a control group and a treatment group as part of a randomized controlled trial. Patients from the population can be randomized into the control and treatment groups with unequal randomization in accordance with a variety of embodiments of the invention. In this example, two new generative models are trained: one for the control group and one for the treatment group. In certain embodiments, control and treatment generative models can be based on a pre-trained generative model but can be additionally trained to reflect new information from the RCT. Outputs from the control and generative models can then be compared to compute the treatment effects. In several embodiments, Bayesian methods and/or the bootstrap may be used to estimate uncertainties in the treatment effects and decision rules based on p-values and/or posterior probabilities may be applied.

Borrowing Information from Digital Subjects

The defining characteristic of a generative model is that one can draw new samples from the model. In several embodiments, each sample from the generative model is a digital subject. Processes in accordance with several embodiments of the invention can draw an initial sample of digital subjects $(y_i, x_{0,i}) \sim p(y_i, x_{0,i})$ for i=1, . . . M' such that the moments of the synthetic population match various moments of the actual population in the RCT. Let $D(\{(y_i, x_{0,i})\}_{i=1}^{M'})$ be a measure of agreement between the moments computed from the digital subject data and the moments computed from the actual population such that the goal is $D(\{(y_i, x_{0,i})\}_{i=1}^{M'})=0$. Processes to generate an initial population in accordance with many embodiments of the invention can choose some i at random and generate a new sample $(y'_i, x'_{0,i}) \sim p(y, x_0)$. Processes can replace digital subject i with the sample if doing so decreases $D(\{(y_i, x_{0,i})\}_{i=1}^{M'})$. For generative models that use a Markov Chain (e.g., Deep Boltzmann Machines) to generate samples, processes in accordance with a number of embodiments of the invention can compute new samples by taking a one or more steps starting at sample i.

Define a variable $s_i=0$ if a given subject is an actual subject from the RCT, and $s_i=1$ if the subject is a digital subject drawn from the generative model. Data from the subjects in the RCT can be represented as $(Y_i, x_{0,i}, w_i, s_i=0)$. Likewise, M samples $(Y_i, x_{0,i}, w_i=0, s_i=1) \sim p_\theta(y^{(0)}, x_0)$ can be generated using the generative model and $N_S \leq M$ of the samples can be selected based on the inclusion criteria of the RCT or to match some of the characteristics of the study population, such as (but not limited to) the means and standard deviations of some chosen variables at time zero.

Systems and methods in accordance with certain embodiments of the invention can incorporate digital subjects into an estimate for the treatment effect by fitting a generalized linear model (GLM) given, in its most general form, by $$g(E[y_i]) = a + \left(b_0 + \sum_j b_j x_{0,i,j}\right) w_i + \left(c_0 + \sum_j c_j x_{0,i,j}\right) s_i + \sum_j d_j x_{0,i,j} \quad (7)$$

in which $g(\cdot)$ is a link function. For example, $g(\mu)=\mu$ corresponds to a linear regression and $g(\mu)=\log(\mu/(1-\mu))$ corresponds to logistic regression. In various embodiments, this framework can also include Cox proportional hazards models used for survival analysis as a special case. In many embodiments, some of these coefficients may be set to zero to create simpler models.

In the example of equation 7, the terms involving the b coefficients represent the treatment effect, which may depend on the baseline covariates $x_0$. The terms involving the c coefficients represent potential bias in the generative model, which may depend on the baseline covariates $x_0$. The terms involving the d coefficients represent potential baseline differences between the treatment and control groups in the trial. The model can be fit using any of a variety of method for fitting GLMs.

In some embodiments, uncertainties in the coefficients can be estimated analytically. Alternatively, or conjunctively, uncertainties in accordance with numerous embodiments of the invention can be estimated using a bootstrap by repeatedly resampling the data (with replacement) and re-fitting the model. Uncertainties in accordance with many embodiments of the invention can be computed as the standard deviations of the coefficients computed by such resampling procedures. Point estimates for the treatment effect and estimates for their uncertainty can be used to perform a hypothesis test in order to create a decision rule in accordance with many embodiments of the invention.

In theory, a perfect generative model will have no bias, with $c_j=0$ for all j so that the indicator variable $s_i$ has no effect. However, machine learning models may not generalize perfectly to data outside of the training set. Typically, the generalization performance of a model is measured by holding out some data from the model training phase so that the held-out data can be used to test the performance of the model. For example, suppose that there are one or more control arms from historical clinical trials in addition to the generative model. Then, the c coefficients can be estimated in accordance with numerous embodiments of the invention by fitting a reduced GLM on the historical control arm data, $$g(E[y_i]) = a + \left(c_0 + \sum_j c_j x_{0,ij}\right) s_i. \quad (8)$$

This can be particularly useful in a Bayesian framework, in which a distribution $\pi(a,c)$ can be estimated for these coefficients using the historical data, where the data-driven prior distribution can be used in a Bayesian analysis (e.g., in Equation 7) in the RCT. Essentially, processes in accordance with some embodiments of the invention can use historical data to determine how well the generative model is likely to generalize to new populations, and then apply this information to the analysis of the RCT. In the limit that $\pi(c) \to \delta(c-0)$, then the digital subjects become substitutable for the actual control subjects in the RCT. As a result, the better the generative model, the fewer control subjects required in the RCT. In certain embodiments, similar approaches could be used to include prior information on any coefficients that are active when $w_i=0$, including the d coefficients for potential baseline differences between the treatment and control groups.

In certain embodiments, simpler models may be created by setting some of the parameters to zero. To understand the effect of the c coefficients, a simple case with linear link functions, no interactions, and setting all d coefficients to zero is described. In this simple case, the GLM above becomes a simple linear regression $$y_i = a + b_0 w_i + c_0 s_i + \epsilon_i. \quad (9)$$

In addition, suppose a prior distribution that can be expressed by adding the following penalty to the log-likelihood function, $$\text{penalty}(c_0) = \frac{\lambda}{2} c_0^2, \quad (10)$$

in which $\lambda$ controls the degree of belief in the quality of the generative model. As mentioned previously, the parameters of the prior distribution could be estimated from historical data and/or specified through some other means. One skilled in the art will recognize that this is not the only choice of prior distribution or means to incorporate prior information, but this provides an example simple enough for analysis to illustrate the properties of processes in accordance with various embodiments of the invention.

In many embodiments, point estimates and uncertainties of the treatment effect can be estimated using a Laplace approximation of the resulting posterior distribution. In practice, various methods including (but not limited to) exact integration, Markov Chain Monte Carlo calculations, and/or variational approximations could be used to obtain a posterior distribution. Using the Laplace approximation (i.e., a series expansion about the maximum of the posterior distribution), it is possible to derive an estimate for the covariance matrix of the posterior distribution of the parameters a, $b_0$, and $c_0$, which can be given by $$\hat{V} = \frac{1}{\lambda N + \lambda N_S + N N_S - (\lambda + N_S) N_T}$$

$$\begin{bmatrix} \lambda + N_S & -(\lambda + N_S) & -N_S \\ -(\lambda + N_S) & N N_S + \lambda(N + N_S) & N_S \\ -N_S & N_S & N + N_S - N_T \end{bmatrix}$$

and the point estimate, which can be given by $$\begin{bmatrix} \hat{a} \\ \hat{b}_0 \\ \hat{c}_0 \end{bmatrix} = \hat{V} \begin{bmatrix} N_T E[y_i | w_i = 1, s_i = 0] + N_C E[y_i | w_i = 0, s_i = 0] + \\ N_S E[y_i | w_i = 0, s_i = 1] \\ N_T E[y_i | w_i = 1, s_i = 0] \\ N_S E[y_i | w_i = 0, s_i = 1] \end{bmatrix}$$

In the limit that $\lambda \to 0$, point estimate $\hat{b}_0 = E[y_i|w_i=1,s_i=0] - E[y_i|w_i=0,s_i=0]$ and uncertainty $$\sigma_{\hat{b}_0}^2 \propto \frac{N}{N_T N_C}.$$

This is the usual frequentist estimate for the treatment effect. Notice that the information from the digital subjects has been completely disregarded because $\lambda=0$ expresses the prior belief that the model used to generate the digital subjects is likely to be of poor quality. By contrast, consider the limit $\lambda \to \infty$ that expresses the prior belief that the digital subjects generated from the model are statistically indistinguishable from actual control subjects. In this case, the point estimate $$\hat{b}_0 = \frac{(N_C + N_S) E[y_i | w_i = 1, s_i = 0] - N_C E[y_i | w_i = 0, s_i = 0] - N_S E[y_i | w_i = 0, s_i = 0]}{N_C + N_S}$$

and uncertainty $$\sigma_{\hat{b}_0}^2 \propto \frac{N + N_S}{N_T(N_C + N_S)}.$$

That is, this treats the digital subject data as if it is exactly substitutable for actual control subject data. Intermediate values of $\lambda$ borrow intermediate amounts of information from the digital control subjects.

By using Bayesian methods to incorporate digital subject data into a clinical trial, as in the previous example, it is possible to increase the statistical power of the trial and/or to reduce the number of actual subjects required for the control group. If the model used to create the digital subjects can be shown to be accurate by estimating the parameters of the prior distribution using historical data, then it can be possible to create and design trials with attractive operating characteristics (i.e., low type-I and type-II error rates) that do not require large numbers of actual subjects. Operating characteristics in accordance with various embodiments of the invention can be characterized through analytical calculations and/or computer simulations.

Figure 5:
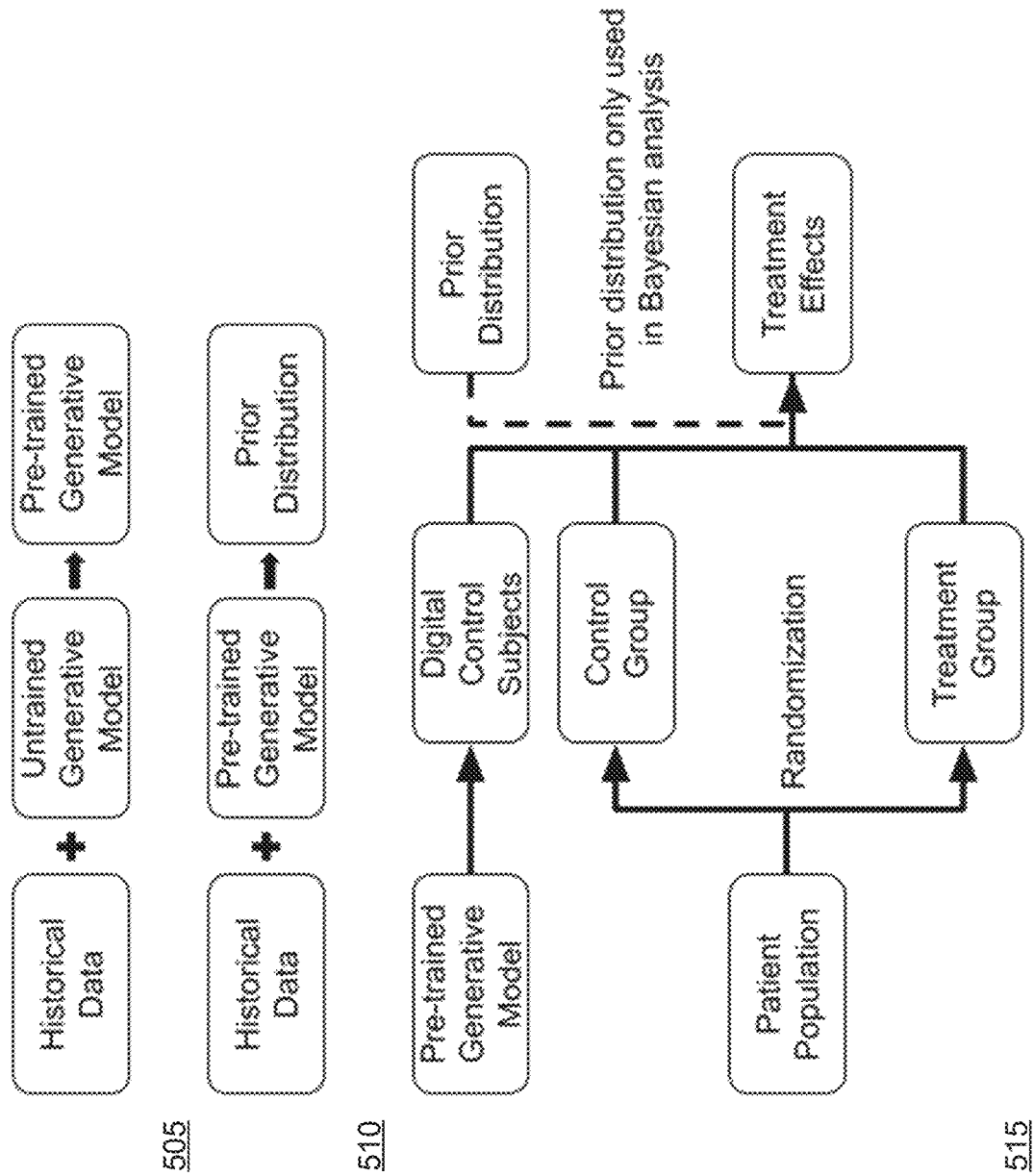
FIG. 5 illustrates an example of borrowing information from digital subjects to estimate treatment effects in accordance with an embodiment of the invention.

An example of borrowing information from digital subjects to estimate treatment effects in accordance with an embodiment of the invention is illustrated in FIG. 5. In the first stage 505, a generative model of the control condition is trained using historical data, such as (but not limited to) data from previously completed clinical trials, electronic health records, or other studies. In the second stage 510, if the analysis to be performed is Bayesian, predictions from the generative model are compared to historical data that were not used to train the model in order to obtain a prior distribution capturing how well the predictions generalize to new populations. A frequentist analysis can skip the second stage 510. In third stage 515, a randomized controlled trial is conducted (potentially with unequal randomization). The generative model is used to create digital subjects, and all of the data are incorporated into a statistical analysis (including the prior from step 510 if the analysis is Bayesian) to estimate the treatment effects. Bayesian methods, analytical calculations, or the bootstrap may be used to estimate uncertainties in the treatment effects, and decision rules based on p-values or posterior probabilities may be applied.

Borrowing Information from Digital Twins

Some methods estimate treatment effects using GLMs while adjusting for covariates. For example, one may perform a regression of the final outcome in the trial against the treatment indicator and a measure of disease severity at the start of the trial. As long as the covariate was measured before the treatment was assigned in a randomized controlled trial, then adjusting for the covariate will not bias the estimate for the treatment effect in a frequentist analysis. When using covariate adjustment, the statistical power is a function of the correlation between the outcome and the covariate being adjusted for; the larger the correlation, the higher the power.

In theory, the covariate that is most correlated with the outcome that one could obtain is an accurate prediction of the outcome. Therefore, another method to incorporate generative models into RCTs in accordance with a variety of embodiments of the invention is to use generative models to predict outcomes and to adjust for the predicted outcomes in a GLM for estimating the treatment effect. Let $E_p[y_i]$ and $Var_p[y_i]$ denote the expected value and variance of the outcome predicted for subject i by the generative model, respectively. Depending on the type of generative model, these moments may be computable analytically or, more generally, by drawing samples from the generative model $p(y_i|x_{0,i})$ and computing Monte Carlo estimates of the moments in accordance with a number of embodiments of the invention. The number of samples used to compute the Monte Carlo estimates can be a parameter selected by the researcher. As above, processes in accordance with several embodiments of the invention can use generative models that generate panel data so that a single generative model may be used for analyses of many outcomes in a given trial (e.g., primary, secondary, and exploratory endpoints as well as safety information). In a number of embodiments, rather than predictions for a given outcome, predictions of multiple outcomes derived from a generative model may all be included in a GLM for a particular outcome. Samples drawn from the generative models in accordance with several embodiments of the invention can be conditioned on the characteristics of a subject at the start of the trial, also referred to as digital twins of that subject.

In many embodiments, digital twins can be incorporated into an RCT in order to estimate the treatment effect by fitting a GLM of the form $$g(E[y_i]) = a + \left(b_0 + \sum_j b_j x_{0,ij}\right) w_i + \left(c_0 + \sum_j c_j x_{0,ij}\right) g(E_p[y_i]) + \sum_j d_j x_{ij} + \left(z_0 + \sum_j z_j x_{0,ij}\right) w_i g(E_p[y_i]) \quad (11)$$

in which $g(\cdot)$ is a link function. For example, $g(\mu)=\mu$ corresponds to a linear regression and $g(\mu)=\log(\mu/(1-\mu))$ corresponds to logistic regression. This framework in accordance with numerous embodiments of the invention can also include Cox proportional hazards models used for survival analysis as a special case. In many embodiments, some of these coefficients may be set to zero to create simpler models. One skilled in the art will recognize that it is trivial to include other predictions from the generative model as covariates if desired.

The above equation can be generalized to various applications and implementations. The terms involving the b coefficients represent the treatment effect, which may depend on the baseline covariates $x_0$. The terms involving the c coefficients represent potential bias in the generative model, which may depend on the baseline covariates $x_0$. The terms involving the d coefficients represent potential baseline differences between the treatment and control groups in the trial. The terms involving the z coefficients reflect that the relationship between the predicted and observed outcomes may be affected by the treatment. The model can be fit using any of a variety of methods for fitting GLMs. In a number of embodiments, uncertainties in the coefficients can be estimated analytically. Alternatively, or conjunctively, processes in accordance with many embodiments of the invention can estimate uncertainties using a bootstrap by repeatedly resampling the data (with replacement) and re-fitting the model; the uncertainties can be the standard deviations of the coefficients computed by this resampling procedure. In some embodiments, point estimates for the treatment effect and estimates for their uncertainty can be used to perform a hypothesis test in order to create a decision rule.

In some embodiments, variances of the outcomes can be modeled through another GLM that adjusts for the variance of the outcome that is predicted by the generative model. For example, variances in accordance with many embodiments of the invention can be modeled as follows $$G(Var[y_i]) = \alpha + \left(\beta_0 + \sum_j \beta_j x_{0,ij}\right) w_i + \left(\gamma_0 + \sum_j \gamma_j x_{0,ij}\right) Gr(Var_p[y_i]) + \sum_j \delta_j x_{ij} + \left(\zeta_0 + \sum_j \zeta_j x_{0,ij}\right) w_i G(Var_p[y_i]) \quad (12)$$

in which $G(\cdot)$ is a link function that is appropriate for the variance. For example, $G(\sigma^2)=\log(\sigma^2)$ can be used for a continuous outcome. In many embodiments, some of these coefficients may be set to zero to create simpler models. One skilled in the art will recognize that other predictions from the generative model can be included as covariates if desired.

Well-trained generative models in accordance with certain embodiments of the invention will have $g(E[y_i]) \approx g(E_p[y_i])$ and $G(\text{Var}[y_i]) \approx G(\text{Var}_p[y_i])$ by construction. Therefore, prior knowledge about the coefficients in the GLMs can be used to improve the estimation of the treatment effect. However, machine learning models may not generalize perfectly to data outside of the training set. Typically, the generalization performance of a model is measured by holding out some data from the model training phase so that the held-out data can be used to test the performance of the model. For example, suppose that there are one or more control arms from historical clinical trials in addition to the generative model. Then, the c coefficients in accordance with various embodiments of the invention can be estimated by fitting a reduced GLM on the historical control arm data, $$g(E[y_i]) = a + \left(c_0 + \sum_j c_j x_{0,i,j}\right) g(E_p[y_i]), \tag{13}$$

for the mean or $$G(\text{Var}[y_i]) = \alpha + \left(\gamma_0 + \sum_j \gamma_j x_{0,i,j}\right) G(\text{Var}_p[y_i]), \tag{14}$$

for the variance. This is particularly useful in a Bayesian framework, in which a distribution $\pi(a,c)$ or $\pi(\alpha,\gamma)$ can be estimated for these coefficients using the historical data, where the data-driven prior distribution can be used in a Bayesian analysis of the RCT. Essentially, this uses the historical data to determine how well the generative model is likely to generalize to new populations, and then applies this information to the analysis of the RCT. In the limit that $\pi(a,c) \to \delta(a-0)\delta(c-1)$, then digital twins in accordance with a variety of embodiments of the invention can become substitutable for actual control subjects in the RCT. As a result, the better the generative model, the fewer control subjects required in the RCT. In some embodiments, similar approaches could be used to include prior information on any coefficients that are active when $w_i=0$, including the d coefficients.

Examples of workflows for frequentist and Bayesian analyses of clinical trials that incorporate digital twins to estimate treatment effects in accordance with various embodiments of the invention are described below. For a frequentist case for a continuous endpoint, consider a simple example $$E[y_i] = a + b_0 w_i + c_0 E_p[y_i] \tag{15}$$

$$\text{Var}[y_i] = \sigma^2 \tag{16}$$

assuming no interactions and homoscedastic errors. One skilled in the art will recognize how this can be applied to the more general case captured by Equation 11 and Equation 12. In numerous embodiments, simple analyses can lead to results that are more easily interpreted. This model implies a normal likelihood, $$y_i \sim \mathcal{N}(a+b_0 w_i+c_0 E_p[y_i], \sigma^2) \tag{17}$$

such that the model can be fit (e.g., by maximum likelihood). There are two situations to consider: (1) the design of the trial has already been determined by some method prior to incorporating the digital twins such that the digital twins can be used to increase the statistical power of the trial, or (2) the trial needs to be designed so that it incorporates digital twins to achieve an efficient design with sufficient power. In the case of a continuous endpoint, the statistical power of the trial will depend on the correlation between $y_i$ and $E_p[y_i]$, which can be estimated from historical data, and is a function of the magnitude of the treatment effect. In a variety of embodiments, analytical formulas can be derived in this special case. Alternatively, or conjunctively, computer simulations can be utilized in the general case.

Once the trial is designed, patients are enrolled and followed until their outcome is measured. In some cases, patients may not be able to finish the trial and various methods (such as Last Observation Carried Forward) need to be applied in order to impute outcomes for the patients who have not finished the trial, as in most clinical trials. In a number of embodiments, GLMs can be fit to the data from the trial to obtain point estimates $\hat{b}_0$ and uncertainties $\hat{\sigma}_{b_0}$ for the treatment effect. The ratio $\hat{b}_0/\hat{\sigma}_{b_0}$ follows a Student's t-distribution which can be used to compute a p-value $p_{b_0}$ and the null-hypothesis that there is no treatment effect can be rejected if $p_{b_0} \leq \mathcal{A}$ in which $\mathcal{A}$ is the desired control of the type-I error rate. This approach is guaranteed to control the type-I error rate, whereas the realized power will be related to the out-of-sample correlation of $y_i$ and $E_p[y_i]$ and the true effect size.

In the Bayesian case for a continuous endpoint with homoscedastic errors, assume a simple analysis, $$E[y_i] = a + b_0 w_i + c_0 E_p[y_i] \tag{18}$$

$$\text{Var}[y_i] = \sigma^2. \tag{19}$$

In certain embodiments, the simple analysis can lead to results that are more easily interpreted. This model implies a normal likelihood, $$y_i \sim \mathcal{N}(a+b_0 w_i+c_0 E_p[y_i], \sigma^2), \tag{20}$$

but processes in accordance with various embodiments of the invention can use a Bayesian approach to fit it instead of the method of maximum likelihood. In particular, with historical data representing the condition $w_i=0$ that was not used to train the generative model, processes in accordance with many embodiments of the invention can fit the model, $$E[y_i] = a + c_0 E_p[y_i] \tag{21}$$

$$\text{Var}[y_i] = \sigma^2. \tag{22}$$

to the historical data in order to derive prior distributions for the analysis of the RCT. To do so, pick a prior distribution $\pi_0(a,c_0,\sigma^2)$ such as (but not limited to) a Normal-Inverse-Gamma prior or another appropriate prior distribution. As there are no data to inform the parameters of the prior before analyzing the historical data, processes in accordance with several embodiments of the invention can use a diffuse or default prior. In numerous embodiments, Bayesian updates to the prior distribution can be computed from the historical data to derive a new distribution $\pi_H(a,c_0,\sigma^2)$, in which the subscript H can be used to denote that this distribution was obtained from historical data. Processes in accordance with numerous embodiments of the invention can then specify a prior distribution $\pi_0(b_0)$ for the treatment effect. This could also be derived from data in accordance with many embodiments of the invention if it's available, or a diffuse or default prior could be used. The full prior distribution is now $\pi_H(a,c_0,\sigma^2)\pi_0(b_0)$. In various embodiments, such distributions can be used compute the expected sample size in order to design the trial, as in a typical Bayesian trial design. Once the trial is designed, patients can be enrolled and followed until their outcome is measured. In some cases, patients may not be able to finish the trial and various methods (such as Last Observation Carried Forward) can be applied in order to impute outcomes for the patients who have not finished the trial, as in most clinical trials.

In numerous embodiments, GLMs can be fit to obtain a posterior distribution $\pi_{RCT}(a,b_0,c_0,\sigma^2)$ for the parameters. A point estimate for the treatment effect can be computed by, for example, $\hat{b}_0 = \int da\, db_0\, dc_0\, d\sigma^2 b_0 \pi_{RCT}(a,b_0,c_0,\sigma^2)$; though, other Bayesian point estimates could be computed as well. In several embodiments, the posterior probability that the treatment effect is greater than zero can also be computed as $\text{Prob}(b_0 \geq 0) = \int da\, db_0\, dc_0\, d\sigma^2 \theta(b_0 \geq 0) \pi^{RCT}(a,b_0,c_0,\sigma^2)$, in which $\theta(\cdot)$ is a logic function that returns one if the argument is true and zero otherwise. As in a typical Bayesian analysis, the treatment can be declared effective if $\text{Prob}(b_0 \geq 0)$ exceeds a pre-specified threshold in accordance with a number of embodiments of the invention.

There are two limits to the Bayesian analysis that can be informative. First, in the limit of a flat prior distribution $\pi_H(a,c_0,\sigma^2)\pi_0(b_0) \propto 1$, then the point estimate and uncertainty for the treatment effect will converge to give the same results as the maximum likelihood method described previously. Thus, if the generalizability of the digital twin model to the population in the RCT is questionable then the Bayesian analysis will end up being very similar to the frequentist analysis. In contrast to the method used to estimate a treatment effect in a trial including digital subjects, including digital twins in the analysis still leads to a gain in power as long as $y_i$ is correlated with $E_p[y_i]$. The other instructive limit is $\pi_H(a,c_0,\sigma^2)\pi_0(b_0) \propto \delta(a-0)\delta(c-1)$. In this limit, the point estimate for the treatment effect converges to $\hat{b}_0 = N_T^{-1} \Sigma_i(y_i - E_p[y_i])w_i$. That is, in some embodiments, the estimate for the treatment effect can be obtained by taking the average of the difference between observed and predicted outcomes for the patients who received the treatment $w_i=1$. Notice that this latter prior distribution can lead to a situation in which the data from the patients who received the control treatment $w_i=0$ can be ignored. Processes in accordance with various embodiments of the invention can run trials without a concurrent control arm.

There are advantages and disadvantages to the frequentist and Bayesian methods that are captured through these simple examples. The frequentist approach to including digital twins in the analysis of an RCT leads to an increase in statistical power while controlling the type-I error rate. If desired, it's also possible to use the theoretical increase in statistical power to decrease the number of subjects required for the concurrent control arm, although this cannot be reduced to zero concurrent control subjects. The Bayesian approach borrows more information about the generalizability of the model used to create the digital twins (e.g., from an analysis of historical data) and, as a result, can increase the power much more than the frequentist approach. In addition, the use of Bayesian methods in accordance with numerous embodiments of the invention can enable one to decrease the size of the concurrent control arm even further. However, the increase in power/decrease in required sample size can come at the cost of an uncontrolled type-I error rate. Therefore, processes in accordance with many embodiments of the invention can perform computer simulations of the Bayesian analysis to estimate the type-I error rate so that the operating characteristics of the trial can be described.

As a final example, it is helpful to consider a simple case in which a GLM is also used for the variance. For example, consider the model $$E[y_i] = a + b_0 w_i + c_0 E_p[y_i] \quad (23)$$

$$\log \text{Var}[y_i] = \alpha + \beta_0 w_i + \gamma_0 \log_p \text{Var}[y_i], \quad (24)$$

which likelihood $$y_i \sim \mathcal{N}(a+b_0 w_i + c_0 E_p[y_i], e^{\alpha + \beta_0 w_i + \gamma_0 \log \text{Var}_p[y_i]}). \quad (25)$$

Models in accordance with a number of embodiments of the invention can allow for heteroscedasticity in which the variance of the outcome is correlated with the variance predicted by the digital twin model, and in which the variance may be affected by the treatment. In several embodiments, a system of GLMs can be fit (e.g., using maximum likelihood, Bayesian approaches, etc.), as was the case for the simpler model. One skilled in the art will clearly recognize that one could also include the interaction or other terms in order to model more complex relationships if necessary. In addition, one skilled in the art will also recognize that including interactions can lead to estimates of conditional average treatment effects in addition to average treatment effects.

Figure 6:
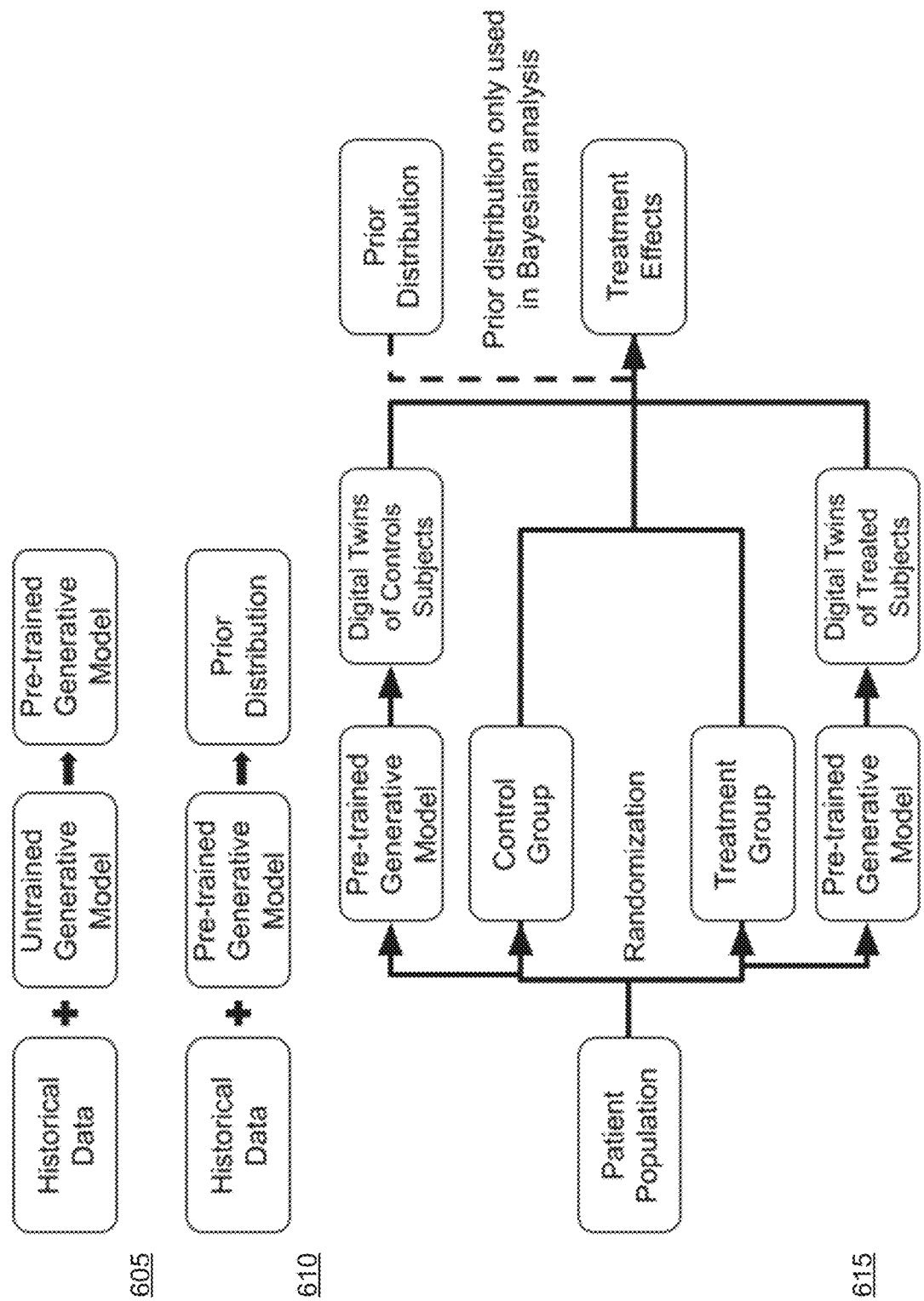
FIG. 6 illustrates an example of borrowing information from digital twins to estimate treatment effects in accordance with an embodiment of the invention.

An example of borrowing information from digital twins to estimate treatment effects in accordance with an embodiment of the invention is illustrated in FIG. 6. In the first part 605, a generative model of the control condition is trained using historical data from previously completed clinical trials, electronic health records, or other studies. In the second part 610, if the analysis to be performed is Bayesian, predictions from the generative model are compared to historical data that were not used to train the model in order to obtain a prior distribution capturing how well the predictions generalize to new populations. A frequentist analysis does not need to obtain a prior distribution. In the third part 615, a randomized controlled trial is conducted (potentially with unequal randomization), digital twins are generated for each subject in the trial, and all of the data are incorporated into a statistical analysis (including the prior from step 610 if the analysis is Bayesian) to estimate the treatment effects. Bayesian methods, analytical calculations, or the bootstrap may be used to estimate uncertainties in the treatment effects, and decision rules based on p-values or posterior probabilities may be applied.

Figure 7:
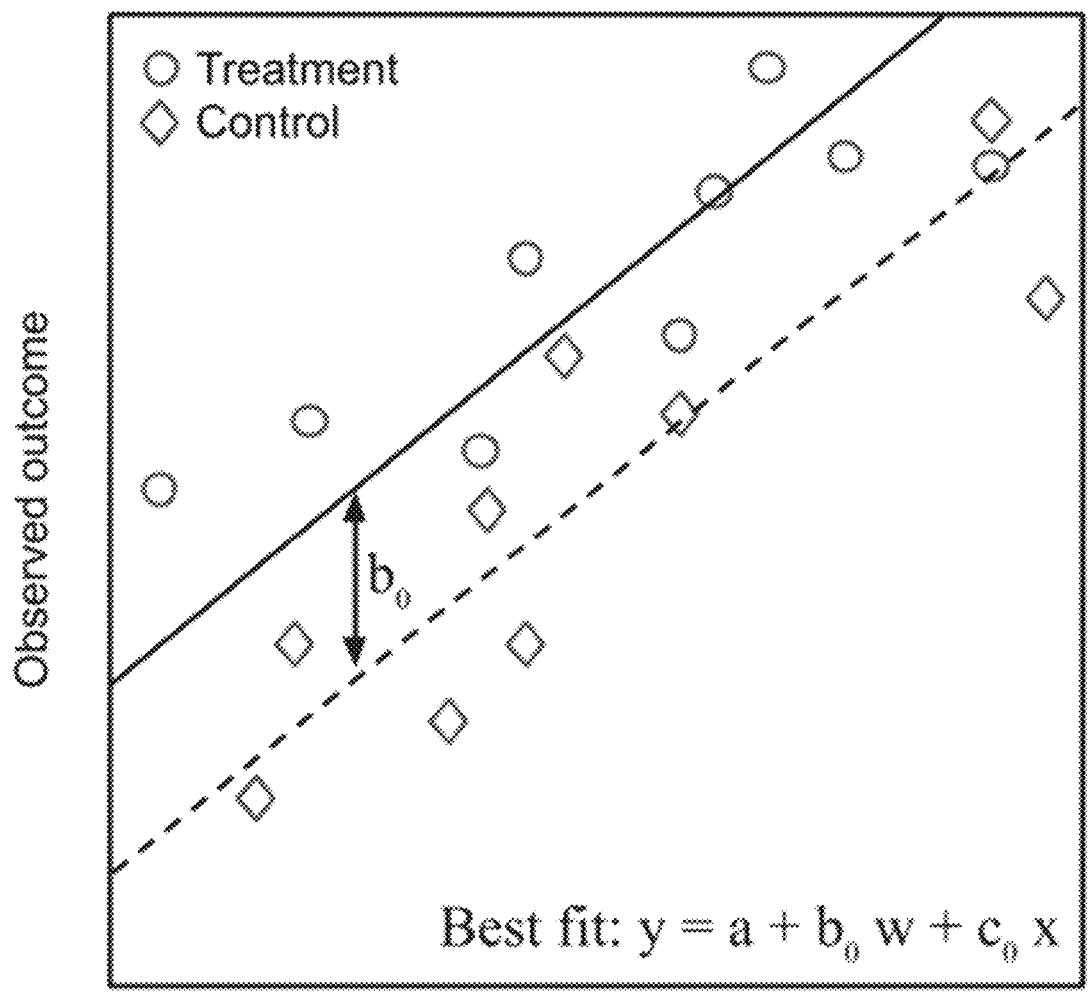
FIG. 7 illustrates an example of using generalized linear models and digital twins estimate treatment effects in accordance with an embodiment of the invention.

An example of using generalized linear models and digital twins estimate treatment effects in accordance with an embodiment of the invention is illustrated in FIG. 7. This drawing illustrates the concept using a simple analysis of a continuous outcome. The x-axis represents the prediction for the outcome from the digital twins, and the y-axis represents the observed outcome of the subjects in the RCT. A linear model is fit to the data from the RCT, adjusting for the outcome predicted from the digital twins. If no interactions are included, then two parallel lines are fit to the data: one to the control group and one to the treatment group. The distance between these lines is an estimate for the treatment effect. Both frequentist and Bayesian methods may be used to analyze the generalized linear model.

Using Generative Models to Define Response and Estimate Treatment Effects

In the previous sections, a response is defined in the units of the outcome, y. For example, an analysis with a survival outcome would produce a treatment effect with the units of time. For example, one may find that the treatment improves survival by 6 months, on average. This is typically useful for aiding interpretation of the treatment effect. However, defining the treatment effect in terms of its natural units may mask important characteristics of the treatment in a population that is heterogeneous. That is, it may be beneficial to measure treatment effects in different ways in order to understand how specific individuals respond to a treatment.

In numerous embodiments, generative models can be used to define individualized responses to treatment. In particular, consider the tail probability of a continuous outcome $$p_i = \int_{y_i}^{\infty} dy \, p(y|x_{0,i}) \quad (26)$$

which defines the probability of observing an outcome greater than or equal to $y_i$ under a generative model of the control condition. That is, there is probability $p_i$ that subject i would have an outcome better than $y_i$ if they had received the control. Note that this example assumes that larger $y_i$ is better, but it is trivial to consider the opposite case by changing the lower limit of integration to $-\infty$ and the upper limit to $y_i$. In several embodiments, $p_i$ can be computed using a Monte Carlo estimate by creating N digital twins with $y_j \sim p(y|x_i)$ for $j=1, \ldots, N$ and approximating $$p_i \approx \frac{1}{N} \Sigma_i \Theta(y_j \geq y_i)$$

in which $\Theta(\cdot)$ is a logical function equal to one if the argument is true and zero otherwise.

Figure 8:
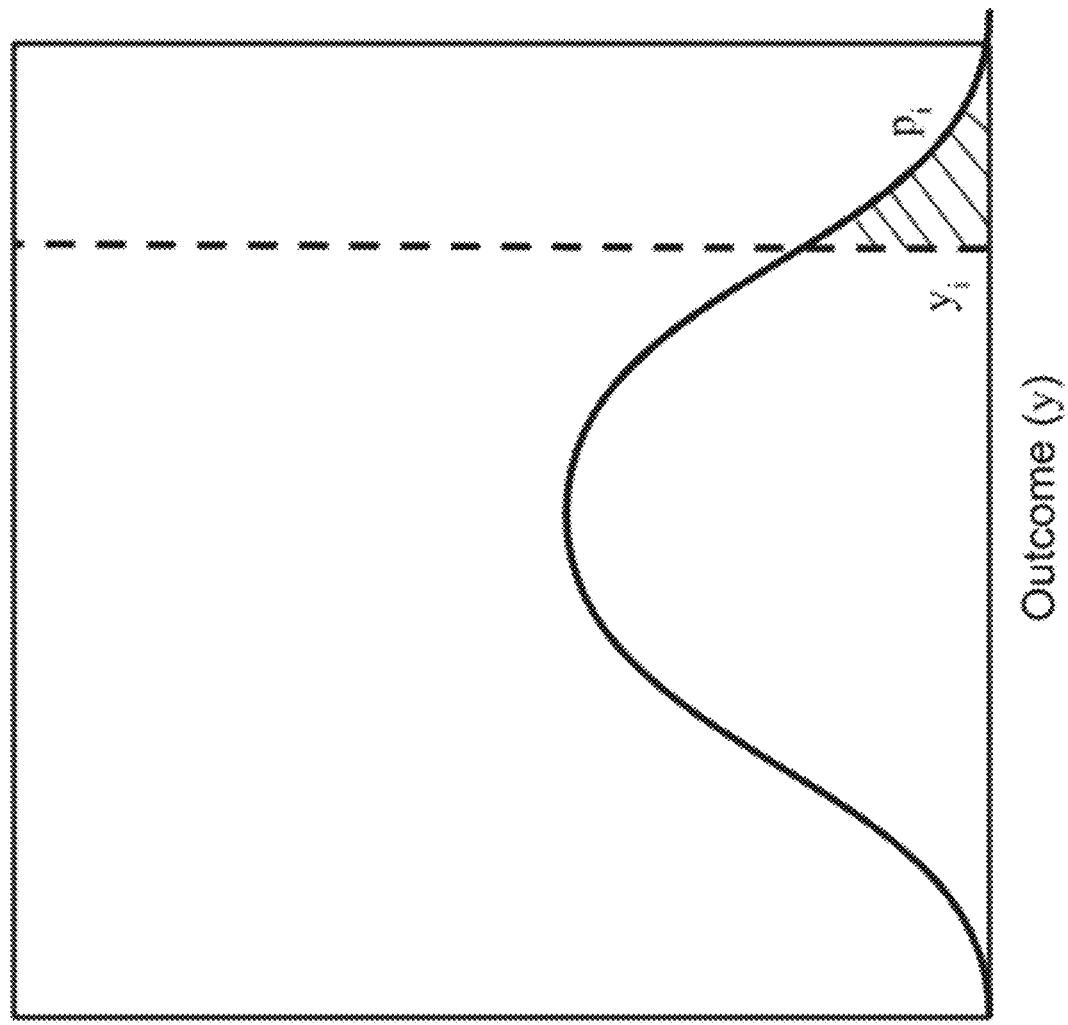
FIG. 8 illustrates an example of using a generative model to measure individual treatment responses in accordance with an embodiment of the invention.

An example of using a generative model to measure individual treatment responses in accordance with an embodiment of the invention is illustrated in FIG. 8. A generative model can be used to compute a tail-area probability for the observed response. This describes how likely it would be for the patient to demonstrate a better response under the control condition than what was observed in the trial.

In the case of a single subject, $p_i$ can be interpreted as a measure of evidence against the null hypothesis that the data were drawn from the generative model. Consider the case of a subject in the control arm with $w_i=0$. There are two reasons why a small $p_i$ may be observed in this case: first, it may simply be due to random chance; second, it may indicate that the generative model of the control condition is biased. This could reflect an improperly trained model or a mismatch between the training data and the concurrent control arm of the RCT. Suppose, however, that $p_i$ is generally large for those subject with $w_i=0$. Then, this indicates that the generative model of the control condition is consistent with the data from the concurrent control arm of the RCT. In this case, if a subject with $w_i=1$ has a small $p_i$ then this could result from either random chance or a response to the treatment.

The intuition described above suggests two additional uses of generative models of the control condition in the analysis of RCT. First, a generative model can be used to measure the discrepancy between a concurrent control arm in an RCT and its expected behavior from historical data. For example, the average surprise $S_C = -\Sigma_i (1-w_i) \log p_i$ is a measure of this discrepancy. A large surprise $S_C$ either indicates a problem with the generative model or a problem with the control group. There are many other ways to combine the $p_i$ for the control group into a score to measure discrepancy. Although this analysis cannot definitively determine the cause of the discrepancy, it can flag potential problems that may merit further investigation by clinical trial sponsors or regulatory authorities.

Processes in accordance with numerous embodiments of the invention can fit a linear model to the data from the RCT using $p_i$ as the measure of response in order to estimate a treatment effect. Processes in accordance with a variety of embodiments of the invention can use a normalizing transform to define the response as $\Phi^{-1}(p_i)$ and fit the linear model $$\Phi^{-1}(p_i) = a + \left(b_0 + \sum_j b_j x_{0,i,j}\right) w_i + \sum_j d_j x_{i,j} + \epsilon_i \quad (27)$$

in which $\Phi^{-1}(\cdot)$ can be the inverse cumulative distribution function of the standard normal distribution. The parameter a accounts for the bias of the generative model. As described in other sections, an informative prior for a can be derived from a regression against historical data in accordance with certain embodiments of the invention. In this case, $\hat{a}=E[\Phi^{-1}(p_i)]$ will be equal to 0 if the generative model is unbiased. In several embodiments, analyses can proceed as described throughout for the frequentist and Bayesian cases with this redefined response. The resulting estimate for the treatment effect has the advantage of being individualized by construction, it describes how much better a particular patient responded compared to their distribution of predicted outcomes under the control condition. However, this also has a disadvantage of being impossible to interpret without referring to the generative model. Nevertheless, such approaches may be particularly useful for treatments with heterogenous effects.

Figure 9:
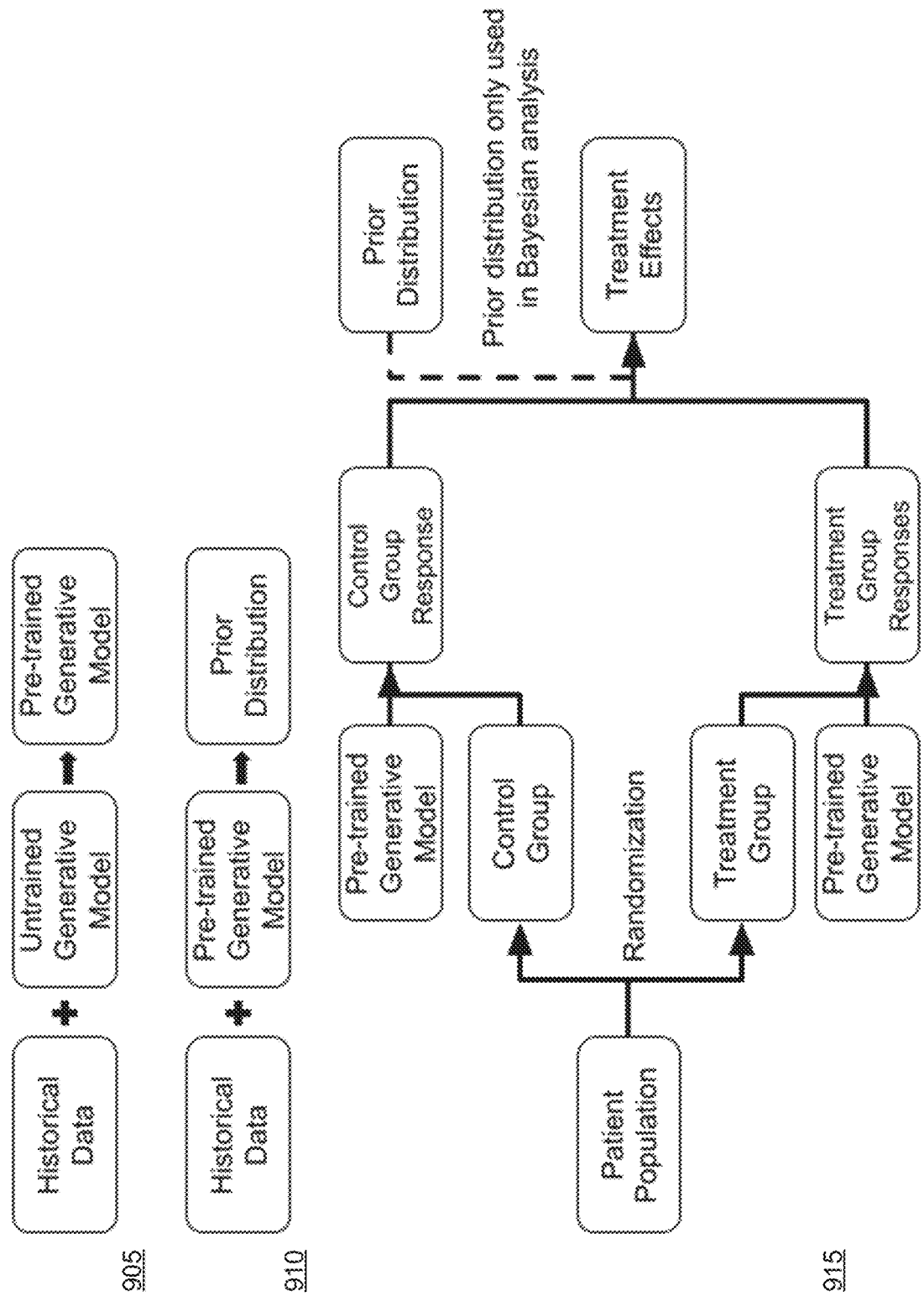
FIG. 9 illustrates an example of estimating treatment effects with individual treatment responses in accordance with an embodiment of the invention.

An example of estimating treatment effects with individual treatment responses in accordance with an embodiment of the invention is illustrated in FIG. 9. In part 905, a generative model of the control condition is trained using historical data from previously completed clinical trials, electronic health records, or other studies. In part 910, if the analysis to be performed is Bayesian, predictions from the generative model are compared to historical data that were not used to train the model in order to obtain a prior distribution capturing how well the predictions generalize to new populations. A frequentist analysis can skip part 910. In part 915, a randomized controlled trial is conducted (potentially with unequal randomization), the generative model is used to define responses for each subject based on transformed tail-area probabilities, and all of the data are incorporated into a statistical analysis (including the prior from step 910 if the analysis is Bayesian) to estimate the treatment effects. Bayesian methods, analytical calculations, or the bootstrap may be used to estimate uncertainties in the treatment effects, and decision rules based on p-values or posterior probabilities may be applied.

Systems for Determining Treatment Effects

Treatment Analysis System

Figure 10:
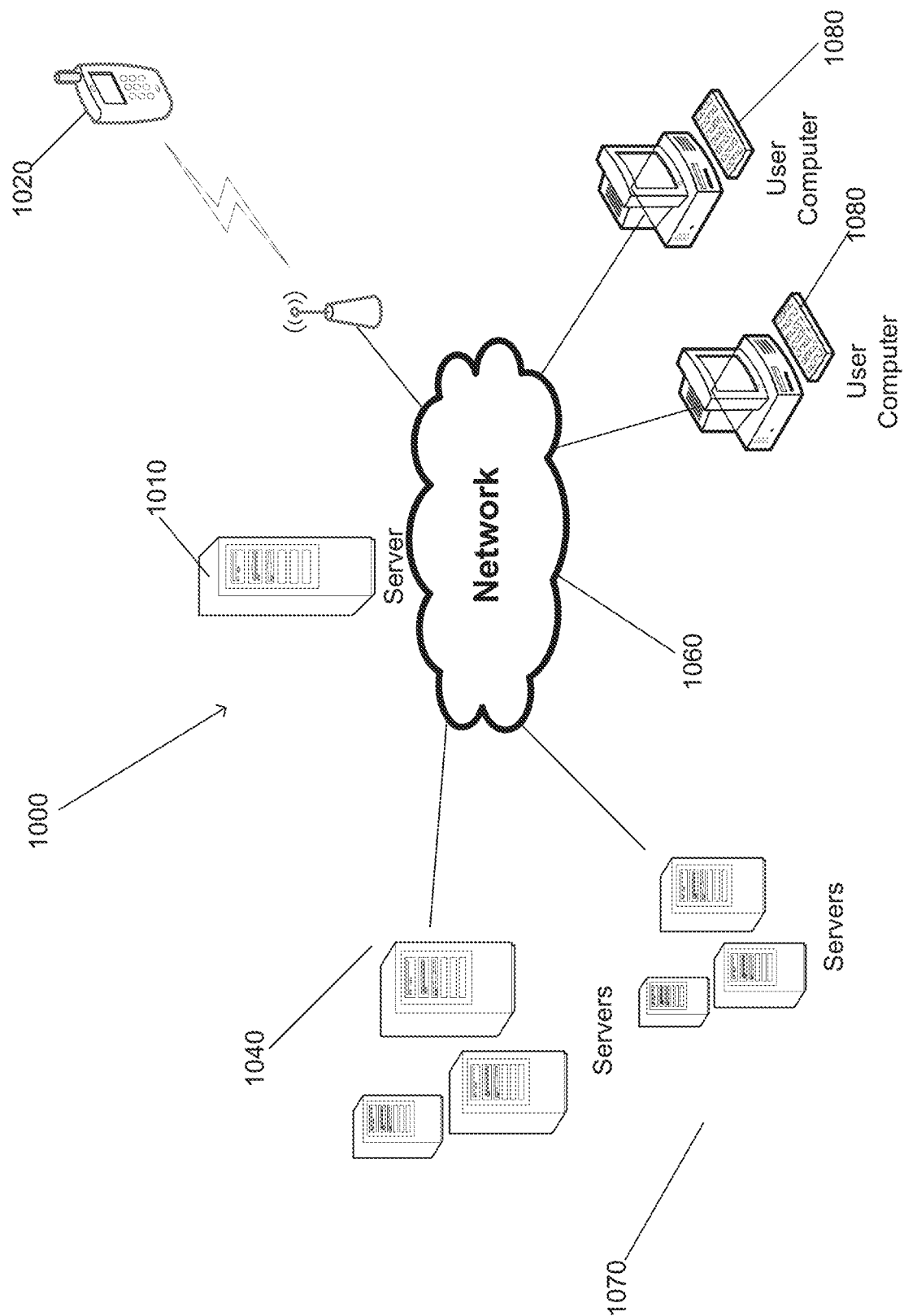
FIG. 10 illustrates an example of a treatment analysis system that determines treatment effects in accordance with some embodiments of the invention.

An example of a treatment analysis system that determines treatment effects in accordance with some embodiments of the invention is illustrated in FIG. 10. Network 1000 includes a communications network 1060. The communications network 1060 is a network such as the Internet that allows devices connected to the network 1060 to communicate with other connected devices. Server systems 1010, 1040, and 1070 are connected to the network 1060. Each of the server systems 1010, 1040, and 1070 is a group of one or more servers communicatively connected to one another via internal networks that execute processes that provide cloud services to users over the network 1060. One skilled in the art will recognize that a treatment analysis system may exclude certain components and/or include other components that are omitted for brevity without departing from this invention.

For purposes of this discussion, cloud services are one or more applications that are executed by one or more server systems to provide data and/or executable applications to devices over a network. The server systems 1010, 1040, and 1070 are shown each having three servers in the internal network. However, the server systems 1010, 1040 and 1070 may include any number of servers and any additional number of server systems may be connected to the network 1060 to provide cloud services. In accordance with various embodiments of this invention, treatment analysis systems in accordance with various embodiments of the invention may be provided by a process being executed on a single server system and/or a group of server systems communicating over network 1060.

Users may use personal devices 1080 and 1020 that connect to the network 1060 to perform processes that determine treatment effects in accordance with various embodiments of the invention. In the shown embodiment, the personal devices 1080 are shown as desktop computers that are connected via a conventional "wired" connection to the network 1060. However, the personal device 1080 may be a desktop computer, a laptop computer, a smart television, an entertainment gaming console, or any other device that connects to the network 1060 via a "wired" connection. The mobile device 1020 connects to network 1060 using a wireless connection. A wireless connection is a connection that uses Radio Frequency (RF) signals, Infrared signals, or any other form of wireless signaling to connect to the network 1060. In FIG. 10, the mobile device 1020 is a mobile telephone. However, mobile device 1020 may be a mobile phone, Personal Digital Assistant (PDA), a tablet, a smartphone, or any other type of device that connects to network 1060 via wireless connection without departing from this invention.

As can readily be appreciated the specific computing system used to determine treatment effects is largely dependent upon the requirements of a given application and should not be considered as limited to any specific computing system(s) implementation.

Treatment Analysis Element

Figure 11:
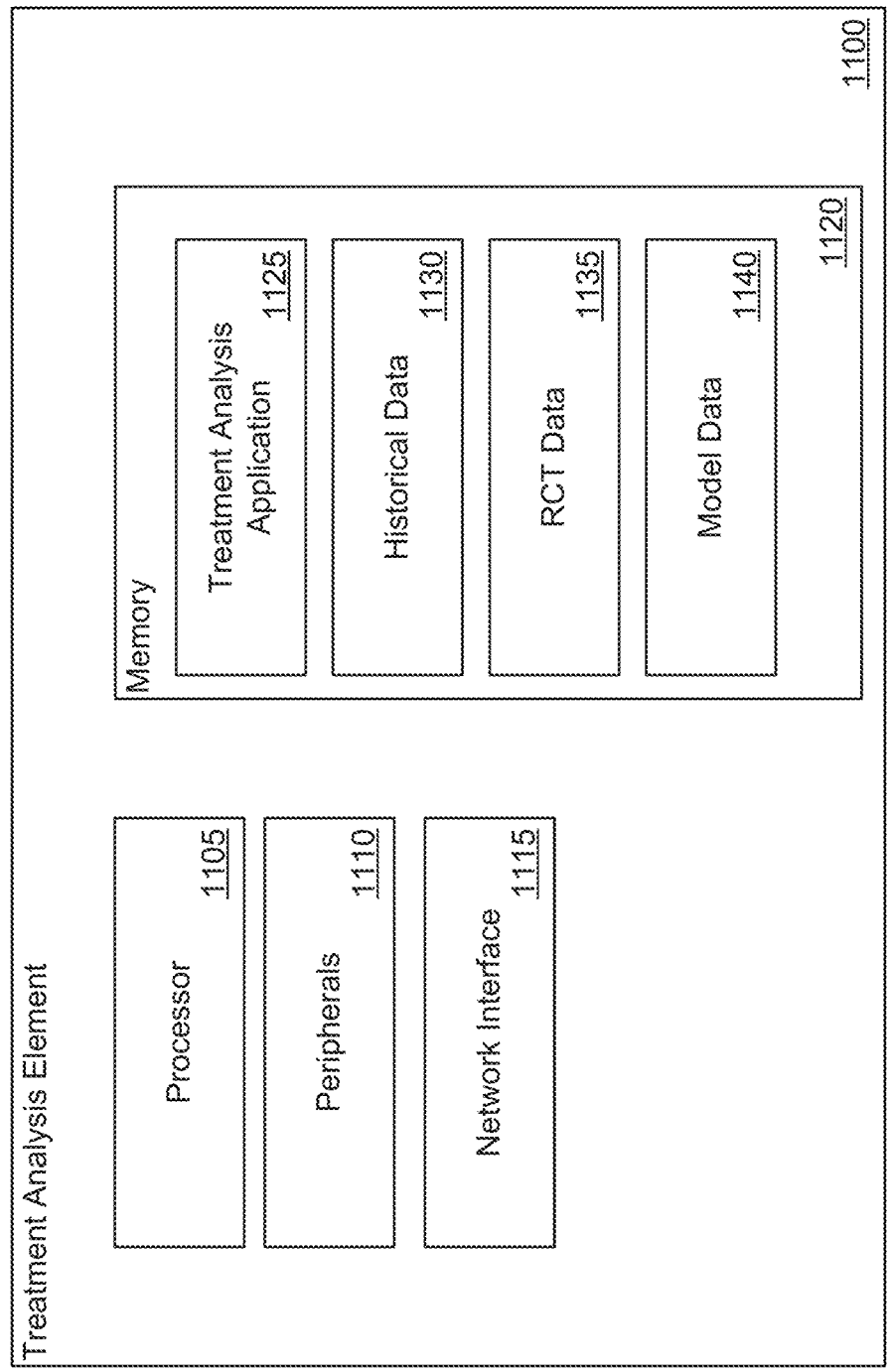
FIG. 11 illustrates an example of a treatment analysis element that executes instructions to perform processes that determine treatment effects in accordance with various embodiments of the invention.

An example of a treatment analysis element that executes instructions to perform processes that determine treatment effects in accordance with various embodiments of the invention is illustrated in FIG. 11. Treatment analysis elements in accordance with many embodiments of the invention can include (but are not limited to) one or more of mobile devices, cloud services, and/or computers. Treatment analysis element 1100 includes processor 1105, peripherals 1110, network interface 1115, and memory 1120. One skilled in the art will recognize that a treatment analysis element may exclude certain components and/or include other components that are omitted for brevity without departing from this invention.

The processor 1105 can include (but is not limited to) a processor, microprocessor, controller, or a combination of processors, microprocessor, and/or controllers that performs instructions stored in the memory 1120 to manipulate data stored in the memory. Processor instructions can configure the processor 1105 to perform processes in accordance with certain embodiments of the invention.

Peripherals 1110 can include any of a variety of components for capturing data, such as (but not limited to) cameras, displays, and/or sensors. In a variety of embodiments, peripherals can be used to gather inputs and/or provide outputs. Treatment analysis element 1100 can utilize network interface 1115 to transmit and receive data over a network based upon the instructions performed by processor 1105. Peripherals and/or network interfaces in accordance with many embodiments of the invention can be used to gather data that can be used to determine treatment effects.

Memory 1120 includes a treatment analysis application 1125, historical data 1130, RCT data 1135, and model data 1140. Treatment analysis applications in accordance with several embodiments of the invention can be used to determine treatment effects of an RCT, to design an RCT, and/or determine decision rules for treatments.

Historical data in accordance with many embodiments of the invention can be used to pre-train generative models to generate potential outcomes for digital subjects and/or digital twins. In numerous embodiments, historical data can include (but is not limited to) control arms from historical control arms, patient registries, electronic health records, and/or real world data. In many embodiments, predictions from the generative model can be compared to historical data that were not used to train the model in order to obtain a prior distribution capturing how well the predictions generalize to new populations.

In some embodiments, RCT data can include panel data collected from subjects of a RCT. RCT data in accordance with a variety of embodiments of the invention can be divided into control and treatment arms based on whether subjects received a treatment. In many embodiments, RCT data can be supplemented with generated subject data. Generated subject data in accordance with a number of embodiments of the invention can include (but is not limited to) digital subject data and/or digital twin data.

In several embodiments, model data can store various parameters and/or weights for generative models. Model data in accordance with many embodiments of the invention can include data for models trained on historical data and/or trained on RCT data. In several embodiments, pre-trained models can be updated based on RCT data to generate digital subjects.

Although a specific example of a treatment analysis element 1100 is illustrated in this figure, any of a variety of treatment analysis elements can be utilized to perform processes for determining treatment effects similar to those described herein as appropriate to the requirements of specific applications in accordance with embodiments of the invention.

Treatment Analysis Application

Figure 12:
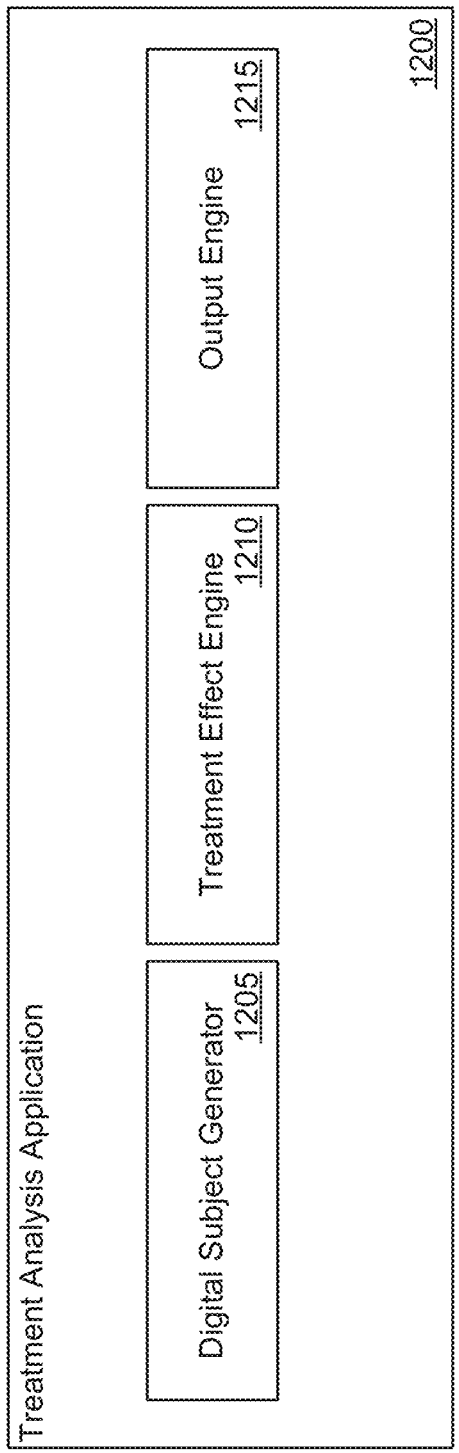
FIG. 12 illustrates an example of a treatment analysis application for determining treatment effects in accordance with an embodiment of the invention.

An example of a treatment analysis application for determining treatment effects in accordance with an embodiment of the invention is illustrated in FIG. 12. Treatment analysis application 1200 includes digital subject generator 1205, treatment effect engine 1210, and output engine 1215. One skilled in the art will recognize that a treatment analysis application may exclude certain components and/or include other components that are omitted for brevity without departing from this invention.

Digital subject generators in accordance with various embodiments of the invention can include generative models that can generate digital subject and/or digital twin data. Generative models in accordance with certain embodiments of the invention can be trained to generate potential outcome data based on characteristics of an individual and/or a population. Digital subject data in accordance with several embodiments of the invention can include (but is not limited to) panel data, outcome data, etc. In several embodiments, generative models can include (but are not limited to) traditional statistical models, generative adversarial networks, recurrent neural networks, Gaussian processes, autoencoders, autoregressive models, variational autoencoders, and/or other types of probabilistic generative models.

In various embodiments, treatment effect engines can be used to determine treatment effects based on generated digital subject data and/or data from a RCT. In some embodiments, treatment effect engines can use digital subject data from digital subject generators to determine a treatment effect in a variety of different applications, such as, but not limited to, comparing separate generative models based on data from the control and treatment arms of a RCT, supplementing a control arm in an RCT, comparing predicted potential control outcomes with actual treatment outcomes, etc. Treatment effects engines in accordance with some embodiments of the invention can be used to determine individualized responses to treatment. In certain embodiments, treatment effect engines can determine biases of generative models of the digital subject generator and incorporate the biases (or corrections for the biases) in the treatment effect analyses.

Output engines in accordance with several embodiments of the invention can provide a variety of outputs to a user, including (but not limited to) decision rules, treatment effects, generative model biases, recommended RCT designs, etc. In numerous embodiments, output engines can provide feedback when the results of generative models of a digital subject generator diverge from the RCT population. For example, output engines in accordance with certain embodiments of the invention can provide a notification when a difference between generated control outcomes for digital twins of subjects from a control arm and their actual control outcomes exceeds a threshold.

Although a specific example of a treatment analysis application is illustrated in this figure, any of a variety of Treatment analysis applications can be utilized to perform processes for determining treatment effects similar to those described herein as appropriate to the requirements of specific applications in accordance with embodiments of the invention.

Although specific methods of determining treatment effects are discussed above, many different methods of treatment analysis can be implemented in accordance with many different embodiments of the invention. It is therefore to be understood that the present invention may be practiced in ways other than specifically described, without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents.

What is claimed is:

1. A method for determining a clinical trial configuration, the method comprising:
    receiving, from a randomized control trial (RCT), RCT data;
    training a set of one or more generative models, wherein at least one of the set of one or more generative models is a neural network trained, at least in part, based on the RCT data;
    generating, using the set of one or more generative models, result data comprising predicted panel data for a set of one or more digital subjects, wherein:
        a digital subject of the set of one or more digital subjects corresponds to a particular subject included in the RCT data; and
        the predicted panel data for the digital subject comprises a plurality of predicted outcomes on characteristics of the digital subject in response to applying a treatment;
    updating, from the predicted panel data and the RCT data, a first predicted outcome of the plurality of predicted outcomes, in response to the treatment;
    computing transformed tail-area probabilities for the digital subject based on the first predicted outcome, wherein the transformed tail-area probabilities correspond to a likelihood for the particular subject to demonstrate a better outcome than the first predicted outcome without the treatment;
    deriving, using a Bayesian analysis on the transformed tail-area probabilities: a point estimate and an uncertainty value for the first predicted outcome;
    determining one or more decision rules for the RCT based, at least in part, on the point estimate and the uncertainty value;
    deriving, based on the one or more decision rules, at least one of:
        a desired type-I error rate for the RCT; or
        a desired type-II error rate for the RCP; and
    using at least one of the desired type-I error rate or the desired type-II error rate to generate a set of trial characteristics for implementing the RCT.

2. The method of claim 1, wherein:
    the RCT data comprises panel data from subjects of the RCT, and
    the panel data describes observed values of multiple characteristics at multiple discrete timepoints.

3. The method of claim 2, wherein:
    the predicted panel data for the set of one or more digital subjects is generated based on population statistics of the RCT; and
    the result data is used to supplement control arm data of the RCT data.

4. The method of claim 2, wherein the predicted panel data for individual digital subjects of the set of one or more digital subjects is generated based on individual characteristics of corresponding subjects of the RCT.

5. The method of claim 4, wherein updating, from the predicted panel data and the RCT data, the first predicted outcome, comprises comparing the predicted panel data based on the particular subject with the panel data for the particular subject from the RCT.

6. The method of claim 1, further comprising receiving a set of historical data, wherein the set of historical data comprises at least one of control arm data from historical control arms, patient registries, electronic health records, or real world data.

7. The method of claim 6, further comprising at least one of:
    pre-training the set of one or more generative models using the set of historical data; or
    determining a prior distribution based on the set of historical data, wherein determining the one or more decision rules is further based on the prior distribution.

8. The method of claim 1, wherein determining the one or more decision rules for the RCT comprises aggregating point estimates corresponding to a plurality of subjects of the RCT data.

9. The method of claim 8, wherein determining the one or more decision rules for the RCT further comprises computing conditional average treatment effects based on the aggregated point estimates.

10. The method of claim 1, further comprising:
    tuning a first generative model of the set of one or more generative models using the RCT data for a control arm of the RCT and a second generative model of the set of one or more generative models using the RCT data for a treatment arm of the RCT,
wherein determining the one or more decision rules comprises comparing the first and second generative models.

11. The method of claim 10, wherein comparing the first and second generative models comprises:
drawing a first set of samples from the first generative model;
drawing a second set of samples from the second generative model; and
comparing distributions of the first and second sets of samples.

12. The method of claim 1, wherein the set of one or more generative models comprises at least one of a Conditional Restricted Boltzmann Machine, a statistical model, a generative adversarial network, a recurrent neural network, a Gaussian process, autoencoders, an autoregressive model, or a variational autoencoder.

13. The method of claim 1, wherein deriving the point estimate and the uncertainty value comprises:
determining a bias for the set of one or more generative models; and
updating the Bayesian analysis based on the bias.

14. The method of claim 1, wherein the set of trial characteristics comprises a number of subjects to be enrolled in each of a control arm and a treatment arm.

15. A non-transitory computer-readable medium comprising instructions that, when executed, are configured to cause a processor to perform a process for determining a clinical trial configuration, the process comprising:
receiving, from a randomized control trial (RCT), RCT data;
training a set of one or more generative models, wherein at least one of the set of one or more generative models is a neural network trained, at least in part, based on the RCT data;
generating, using the set of one or more generative models, result data comprising predicted panel data for a set of one or more digital subjects, wherein:
a digital subject of the set of one or more digital subjects corresponds to a particular subject included in the RCT data; and
the predicted panel data for the digital subject comprises a plurality of predicted outcomes on characteristics of the digital subject in response to applying a treatment;
updating, from the predicted panel data and the RCT data, a first predicted outcome of the plurality of predicted outcomes, in response to the treatment;
computing transformed tail-area probabilities for the digital subject based on the first predicted outcome, wherein the transformed tail-area probabilities correspond to a likelihood for the particular subject to demonstrate a better outcome than the first predicted outcome without the treatment;
deriving, using a Bayesian analysis on the transformed tail-area probabilities: a point estimate and an uncertainty value for the first predicted outcome;
determining one or more decision rules for the RCT based, at least in part, on the point estimate and the uncertainty value;
deriving, based on the one or more decision rules, at least one of:
a desired type-I error rate for the RCT; or
a desired type-II error rate for the RCP; and
using at least one of the desired type-I error rate or the desired type-II error rate to generate a set of trial characteristics for implementing the RCT.

16. The non-transitory computer-readable medium of claim 15, wherein:
the RCT data comprises panel data from subjects of the RCT, and
the panel data describes observed values of multiple characteristics at multiple discrete timepoints.

17. The non-transitory computer-readable medium of claim 16, wherein:
the predicted panel data for the set of one or more digital subjects is generated based on at least one of:
population statistics of the RCT; or
individual characteristics of corresponding subjects of the RCT; and
the result data is used to supplement control arm data of the RCT data.

18. The non-transitory computer-readable medium of claim 17, updating, from the predicted panel data and the RCT data, the first predicted outcome, comprises comparing the predicted panel data based on the particular subject with the panel data for the particular subject from the RCT.

19. The non-transitory computer-readable medium of claim 15, further comprising:
receiving a set of historical data, wherein the set of historical data comprises at least one of control arm data from historical control arms, patient registries, electronic health records, or real world data; and
performing at least one of:
pre-training the set of one or more generative models using the set of historical data; or
determining a prior distribution based on the set of historical data, wherein determining the one or more decision rules is further based on the prior distribution.

20. The non-transitory computer-readable medium of claim 15, wherein the set of trial characteristics comprises a number of subjects to be enrolled in each of a control arm and a treatment arm.

* * * * *